(12) United States Patent
Akella et al.

(10) Patent No.: US 9,464,053 B2
(45) Date of Patent: *Oct. 11, 2016

(54) COMPOSITIONS FOR REDUCING Aβ 42 PRODUCTION AND THEIR USE IN TREATING ALZHEIMER'S DISEASE (AD)

(71) Applicant: KAREUS THERAPEUTICS SA, La Chaux-de-Fonds (CH)

(72) Inventors: Venkateswarlu Akella, Hyderabad (IN); Uday Saxena, Atlanta, GA (US); Anji Reddy Kallam, Hyderabad (IN)

(73) Assignee: KAREUS THERAPEUTICS, SA, La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/469,366

(22) Filed: Aug. 26, 2014

(65) Prior Publication Data

US 2014/0364457 A1 Dec. 11, 2014

Related U.S. Application Data

(63) Continuation of application No. 13/574,886, filed as application No. PCT/IB2011/050290 on Jan. 22, 2011, now Pat. No. 8,846,721.

(60) Provisional application No. 61/395,702, filed on May 17, 2010.

(30) Foreign Application Priority Data

Jan. 25, 2010 (IN) .......................... 198/MUM/2010

(51) Int. Cl.
*C07D 213/80* (2006.01)
*C07D 401/06* (2006.01)
*A61K 31/44* (2006.01)
*C07D 213/82* (2006.01)
*C07D 213/56* (2006.01)
*C07D 401/12* (2006.01)

(52) U.S. Cl.
CPC ........... *C07D 213/82* (2013.01); *C07D 213/56* (2013.01); *C07D 213/80* (2013.01); *C07D 401/06* (2013.01); *C07D 401/12* (2013.01)

(58) Field of Classification Search
None
See application file for complete search history.

(56) References Cited

U.S. PATENT DOCUMENTS 8,846,721 B2 * 9/2014 Akella et al. ................. 514/343

OTHER PUBLICATIONS

Wu et al, Toxicology, vol. 236, 2007, pp. 1-6.*

* cited by examiner

*Primary Examiner* — Zinna Northington Davis
(74) *Attorney, Agent, or Firm* — Bryan D. Zerhusen; Locke Lord LLP

(57) ABSTRACT

Novel small molecule compounds for reduction of Aβ 42 production and for treatment of Alzheimer's disease and other neurodegenerative disorders, methods of making them and pharmaceutical compositions containing them are described.

8 Claims, 5 Drawing Sheets

**P<0.01, *P<0.05 Vs familiar object (Paired *t*-test)

*P<0.001, P<0.01 Vs familiar object (Paired *t*-test)

COMPOSITIONS FOR REDUCING Aβ 42 PRODUCTION AND THEIR USE IN TREATING ALZHEIMER'S DISEASE (AD)

CROSS-REFERENCE TO RELATED APPLICATIONS

The present disclosure is entitled to the benefit under 35 U.S.C. §§120 and 365(c) as a continuation-in-part of U.S. patent application Ser. No. 13/574,886, filed: 24 Jul. 2012, entitled: Compositions For Reducing Aβ 42 Production and Their Use in Treating Alzheimer's Disease (AD); which is the National Stage of International Patent Application PCT/IB2011/050290, filed: 22 Jan. 2011, entitled: Novel Compositions For Reducing Aβ 42 Production and Their Use in Treating Alzheimer's Disease (AD); which claims the benefit of priority to Indian Patent Application Serial No. 198/MUM/2010, filed 25 Jan. 2010, and U.S. Provisional Patent Application Ser. No. 61/395,702 filed 17 May 2010, the disclosures of which are hereby incorporated herein by reference in their entirety for all purposes.

FIELD OF THE INVENTION

Described are small molecule compounds, which reduce the production of Aβ42 and can be used to treat AD, dementia and other neurodegenerative disorders such as ischemic stroke, Parkinson's disease, methods of making the small molecules and pharmaceutical compositions containing them.

BACKGROUND

Alzheimer's disease (AD) is a degenerative central nervous system disorder associated with extensive loss of specific neuronal cells, and characterized clinically by progressive loss of memory, cognition, reasoning, judgment and emotional stability that gradually leads to profound mental deterioration and ultimately death. The disease currently affects as many as four million individuals in the United States alone. To date, there is no treatment that stops or reverses the disease and it presently causes up to 100,000 deaths annually.

AD is characterized by excessive production of small hydrophobic peptides called amyloid beta peptides (Aβ peptides) with Aβ42 peptide being particularly neurotoxic leading to pathogenesis of this disease. The brains of individuals with AD exhibit neuronal degeneration and characteristic lesions variously referred to as amyloid plaques and neurofibrillary tangles. Currently, the only definitive diagnosis of AD is the presence of these plaques in post-mortem brains. According to the dominant scientific hypothesis for AD, called amyloid cascade or amyloid hypothesis, it is believed that progressive cerebral deposition of particular amyloidogenic peptides, beta-amyloid peptides, play a detrimental role in the pathogenesis of AD and can precede cognitive symptoms and onset of dementia by years or possibly even decades (Hardy J, Selkoe D J, Science. 2002 297(5580): 353-6). Thus prevention of production of these peptides has become the major focus of pharmaceutical industry approaches to treatment of AD.

The Aβ peptides are produced as a result of excessive processing of the amyloid precursor protein (APP), the parent trans-membrane protein found in neurons and other cells (Selkoe, D J. Trends Cell Biol. 1998, 8(11):447-53). Amyloid plaques are composed primarily of 40 and 42 amino acid peptides (called Aβ40 and Aβ42, respectively) derived from amyloid precursor protein (APP) by sequential proteolysis catalyzed by the aspartyl protease, beta-secretase, followed by presenilin-dependent gamma-secretase cleavage. Aβ42 is more hydrophobic and less soluble than Aβ40 and is the predominant species in amyloid plaques. Aβ42 is more prone to aggregation and deposition and therefore the cause of neurotoxicity as well as synaptic loss. Therefore all attention for drug development is focused on inhibiting Aβ42 production rather than any other beta amyloid peptide species (Selkoe D J, Schenk D. Annu Rev Pharmacol Toxicol. 2003; 43:545-84).

Yet another related condition is Multiple Sclerosis (MS). Multiple sclerosis (MS) involves an immune-mediated process in which an abnormal response of the body's immune system is directed against the central nervous system (CNS), which is made up of the brain, spinal cord and optic nerves. The exact antigen—or target that the immune cells are sensitized to attack—remains unknown, which is why MS is considered by many experts to be "immune-mediated" rather than "autoimmune." As per an estimate by National MS Society of US, more than 2.3 million people are affected by Multiple Sclerosis worldwide. As per the recommendation of the National Multiple Sclerosis Society, the patients should be considered for treatment with one of the FDA-approved "disease-modifying" drugs as soon as possible following a definite diagnosis of MS with active or relapsing disease. These medications help to reduce inflammation in the CNS, reduce the frequency and severity of MS attacks and the numbers of lesions in the CNS, and may slow the progression of disability.

There are many reasons and risk factors, which may trigger excessive production of Aβ42. In particular ageing, head injury/trauma, genetics such as Apo E4/4 carriers, cardiovascular disease and type 2 diabetes may all predispose an individual towards higher production of Aβ42 and therefore onset of Alzheimer's disease. Two molecular events, which may be closely tied to enhanced Aβ42 production and the onset, progression and pathogenesis of the disease are generation of reactive oxygen species (ROS) and reduced energy production by neurons (Moreira P I et al., CNS Neurol. Disord. Drug Targets. 2008; 7:3-10). The generation of ROS and consequent cellular damage/response is thought to contribute too much of the hallmark AD pathology seen in susceptible neurons. Defects in energy production by neurons are observed very early in the disease process. Energy deficits in neuron are defined as a reduction in synthesis of ATP, the molecular form of energy in cells.

There are no known drugs or small molecule compounds which target both of these events, i.e. neuronal oxidative stress and energy deficiency as a method to reduce Aβ42 production and as treatment for his disease.

SUMMARY

The present description relates to the surprising and unexpected discovery of pyridine carboxylic acid derivatives, which are capable of inhibiting/reducing the production of Aβ in cells. As such, we describe a series of compounds, which target both the generation of reactive oxygen species (ROS) and reduced energy production by neurons simultaneously, and show that such a compound can reduce Aβ42 production and also improve cognition in an animal model of disease.

Thus, in one aspect, the present description provides compounds of formula (I):

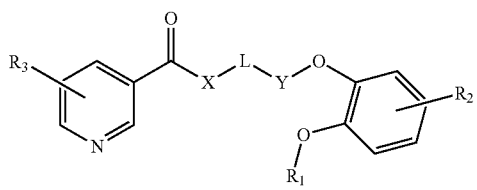

(I)

or a pharmaceutically acceptable salt, prodrug or stereoisomer thereof, wherein:

X can be selected from O, NR", S, or substituted or unsubstituted alkylene;

L can be a bond, or substituted or unsubstituted alkylene, preferably substituted or unsubstituted C1-4 alkylene and preferably substituents can be selected from Ra;

X and L together with their attached positions can be formed a substituted or unsubstituted cycloalkyl or a substituted or unsubstituted heterocyclyl;

Y can be a bond, —C(O)—, —S(O)$_2$—, NR", or substituted or unsubstituted alkylene, $R_1$ can be H, substituted or unsubstituted alkyl, or substituted or unsubstituted cycloalkyl;

$R_2$, can be selected from H, (CH2)nOR', substituted or unsubstituted alkyl, substituted or unsubstituted alkenyl, substituted or unsubstituted alkanoyl, substituted or unsubstituted aryl, substituted or unsubstituted aralkyl, substituted or unsubstituted heterocyclyl, or substituted or unsubstituted cycloalkyl;

R3 can be H, OH, halogen, NR", C(O)$_2$R", C(O)NR", substituted or unsubstituted alkyl, substituted or unsubstituted alkoyl, or substituted or unsubstituted cycloalkyl;

Ra can be H, OR', C(O)$_2$R', C(O)R', NR', N(NR")NR', SR', SO$_2$R', SO$_2$NR', NSO$_2$R', C(O)NR', (CH2)$_n$OR', (CH2)$_n$SR', substituted or unsubstituted alkyl, substituted or unsubstituted aryl, substituted or unsubstituted cycloalkyl, or substituted or unsubstituted heterocyclyl;

n can be an integer 0-5; and

R' and R" are independently can be selected from H, substituted or unsubstituted alkyl, substituted or unsubstituted aryl, substituted or unsubstituted cycloalkyl, or substituted or unsubstituted heterocyclyl.

In an additional aspect, the description also provides the process for making the compounds of formula (I).

In another aspect, the description provides a compound of Formula II:

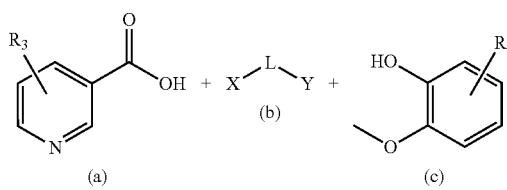

(II)

or a combination thereof which comprises all the three components (a), (b) and (c), wherein:

X is selected from 0, and NR";

L is a bond, or a substituted or unsubstituted C1-4 alkylene, wherein the substituents are selected from Ra;

X and L together with their attached positions form a five membered heterocyclyl, where in heterocyclyl is

Y is a bond, —C(O)—, or —S(O)$_2$—;

$R_2$, is selected from H or C2-C3 alkenyl;

$R_3$ is H;

Ra is selected from H, OR', C(O)2R', C(O)R', NR', N(NR")NR', SR', SO2R', SO2NR', NSO2R', C(O)NR', (CH2)nOR', (CH2)nSR', substituted or unsubstituted C1-C6 alkyl, wherein substituent is selected from OMe, S-Me, isopropyl, isobutyl —(CH2)n-Ph, —(CH2)n-Ph-OMe or —(CH2)n-indole,

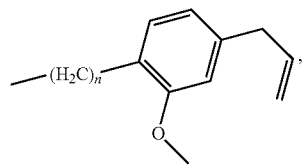

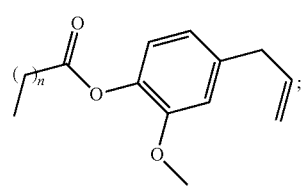

and n is an integer 0-5.

In yet another aspect, the description provides a compound of Formula III:

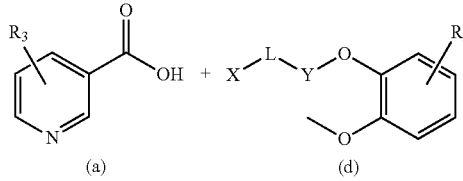

(III)

comprising components (a) and (d), and a compound of Formula IV:

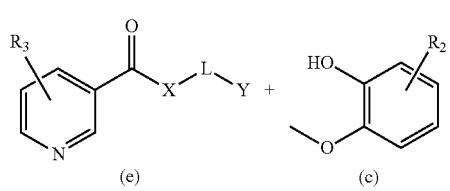

(IV)

comprising components (e) and (c).

In certain embodiments, component (e) is:

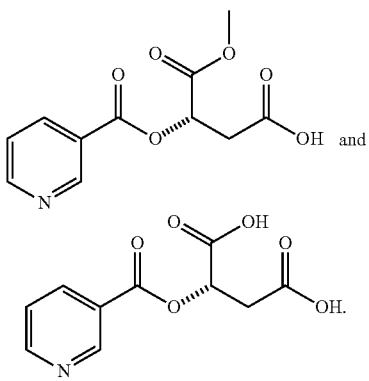

In certain additional embodiments, component (e) is:

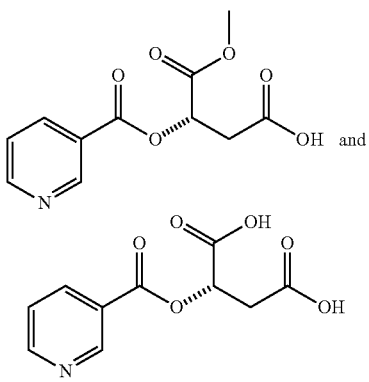

The present description also provides a pharmaceutical composition comprising a therapeutically effective amount of a compound or combination of compounds as described herein, or a pharmaceutically acceptable salt form, stereoisomer or a prodrug of formula (I) and a pharmaceutically acceptable carrier.

The present description further provides compounds useful for treating or lessening severity of Alzheimer's disease (AD), dementia and other neurodegenerative diseases such as multiple sclerosis (MS), ischemic stroke and Parkinson's disease, Fragile X Syndrome, Amyotropic Lateral Sclerosis (ALS), Huntington's disease.

The present description further provides methods of treating or lessening severity of Alzheimer's disease (AD), dementia and other neurodegenerative diseases such as multiple sclerosis (MS), ischemic stroke and Parkinson's disease, Fragile X Syndrome, Amyotropic Lateral Sclerosis (ALS), Huntington's disease wherein said method comprises administering to a patient a compound of the present invention or composition thereof.

Pharmaceutically acceptable salts of the compounds of the formula (I) are also contemplated. Likewise, pharmaceutically acceptable solvates, including hydrates, of the compounds of the formula (I) are contemplated.

It should be understood that the formula (I) structurally encompasses all stereo isomers, including enantiomers and diastereomers, which may be contemplated from the chemical structure of the genus described herein.

Also contemplated are prodrugs of the compounds of the formula (I).

According to one embodiment, there is provided a compound of formula (I), wherein X is O.

According to one embodiment, there is provided a compound of formula (I), wherein X is N.

According to one embodiment, there is provided a compound of formula (I), wherein L is a bond.

According to one embodiment, there is provided a compound of formula (I), wherein L is substituted or unsubstituted alkylene.

According to one embodiment, there is provided a compound of formula (I), wherein Y is —C(O)—.

According to one embodiment, there is provided a compound of formula (I), wherein R1 is substituted or unsubstituted alkyl.

According to one embodiment, there is provided a compound of formula (I), wherein R2 is H, substituted or unsubstituted alkyl, $CH_2CH=CH_2$.

According to one embodiment, there is provided a compound of formula (I), wherein R3 is H.

According to one embodiment, there is provided a compound of formula (I), wherein X and L together with their attached positions can be forming a substituted or unsubstituted heterocyclyl.

According to one embodiment, there is provided a compound of formula (I), wherein Ra is H, substituted or unsubstituted alkyl, $C(O)_2R'$, $-C_3H_6SCH_3$, substituted or unsubstituted phenyl, substituted or unsubstituted benzyl, and substituted or unsubstituted heterocyclyl.

According to one embodiment, there is provided a compound of formula (I), wherein n is 3.

According to one embodiment, there is provided a compound of formula (I), wherein R' and R" are independently selected from H, $CH_3$, and 4-allyl-6-methoxyphenyl.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
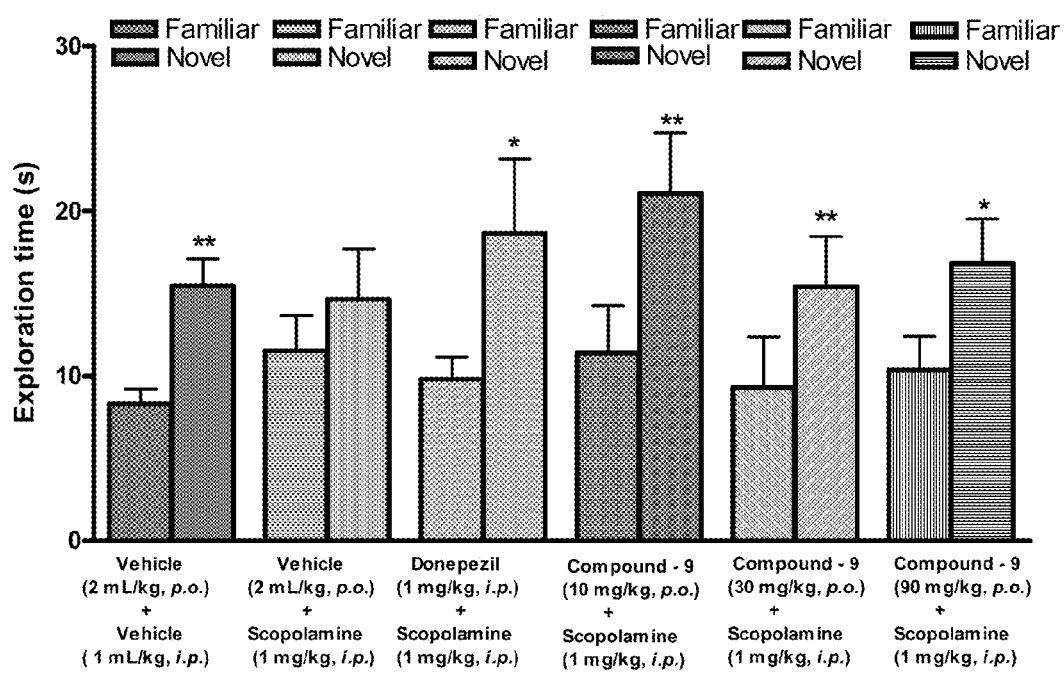
FIG. 1: Effect of compound 9 in improving cognitive function in rat novel object recognition test. Mean (±S.E.M) effect of vehicle (2 mL/kg, p.o.)+vehicle (1 mL/kg, i.p.), vehicle (2 mL/kg, p.o.)+Scopolamine (1 mg/kg, i.p.), Donepezil (1 mg/kg, i.p.)+Scopolamine (1 mg/kg, i.p.), Compound-9 (10 mg/kg, p.o.)+Scopolamine (1 mg/kg, i.p.), Compound-9 (30 mg/kg, p.o.)+Scopolamine (1 mg/kg, i.p.) and Compound-9 (90 mg/kg, p.o.)+Scopolamine (1 mg/kg, i.p.) on time spent exploring the novel and familiar object.

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

Thus, in one aspect, the present description is directed to compounds of formula (I)

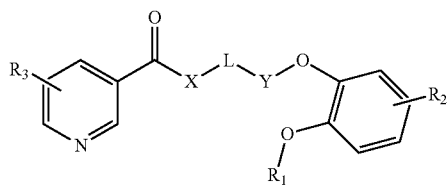

(I)

or a pharmaceutically acceptable salt, prodrug or stereoisomer thereof,
wherein:
X can be selected from O, NR", S, or substituted or unsubstituted alkylene;
L can be a bond, or substituted or unsubstituted alkylene, preferably substituted or unsubstituted C1-4 alkylene and preferably substituents can be selected from Ra;
X and L together with their attached positions can be formed a substituted or unsubstituted cycloalkyl or a substituted or unsubstituted heterocyclyl;
Y can be a bond, —C(O)—, —S(O)$_2$—, NR", or substituted or unsubstituted alkylene,
$R_1$ can be H, substituted or unsubstituted alkyl, or substituted or unsubstituted cycloalkyl;
$R_2$ can be selected from H, (CH$_2$)nOR', substituted or unsubstituted alkyl, substituted or unsubstituted alkenyl, substituted or unsubstituted alkanoyl, substituted or unsubstituted aryl, substituted or unsubstituted aralkyl, substituted or unsubstituted heterocyclyl, or substituted or unsubstituted cycloalkyl;
$R_3$ can be H, OH, halogen, NR", C(O)$_2$R", C(O)NR", substituted or unsubstituted alkyl, substituted or unsubstituted alkoyl, or substituted or unsubstituted cycloalkyl;

Ra can be H, OR', C(O)$_2$R', C(O)R', NR', N(NR")NR', SR', S(O)$_2$R', S(O)$_2$NR', NS(O)$_2$R', C(O)NR', (CH2)$_n$OR', (CH2)nSR', substituted or unsubstituted alkyl, substituted or unsubstituted aryl, substituted or unsubstituted cycloalkyl, or substituted or unsubstituted heterocyclyl;
n can be an integer 0-5; and
R' and R" are independently can be selected from H, substituted or unsubstituted alkyl, substituted or unsubstituted aryl, substituted or unsubstituted cycloalkyl, or substituted or unsubstituted heterocyclyl.

The present description also provides the process for making the compounds of formula (I).

The present description also provides a pharmaceutical composition comprising a therapeutically effective amount of a compound or combination of compounds of the present invention, or a pharmaceutically acceptable salt form, stereoisomer and a pharmaceutically acceptable carrier.

The present description further provides compounds useful for treating or lessening severity of Alzheimer's Disease (AD), dementia and other neurodegenerative diseases such as ischemic stroke, Parkinson's disease The present description further provides methods of treating or lessening severity of Alzheimer's disease (AD), dementia and other neurodegenerative diseases such as ischemic stroke, Parkinson's disease wherein said method comprises administering to a patient a compound as described herein or a composition comprising the same.

Pharmaceutically acceptable salts of the compounds of the formula (I) are also contemplated. Likewise, pharmaceutically acceptable solvates, including hydrates, of the compounds of the formula (I) are contemplated.

It should be understood that the formula (I) structurally encompasses all stereo isomers, including enantiomers, polymorphs, crystal forms and diastereomers, which may be contemplated from the chemical structure of the genus described herein.

Also contemplated are prodrugs of the compounds of the formula (I).

According to one embodiment, there is provided a compound of formula (I), wherein X is O.

According to one embodiment, there is provided a compound of formula (I), wherein X is N.

According to one embodiment, there is provided a compound of formula (I), wherein L is a bond.

According to one embodiment, there is provided a compound of formula (I), wherein L is substituted or unsubstituted alkylene.

According to one embodiment, there is provided a compound of formula (I), wherein Y is —C(O)—.

According to one embodiment, there is provided a compound of formula (I), wherein $R_1$ is substituted or unsubstituted alkyl.

According to one embodiment, there is provided a compound of formula (I), wherein $R_2$ is H, substituted or unsubstituted alkyl, CH$_2$CH=CH$_2$.

According to one embodiment, there is provided a compound of formula (I), wherein $R_3$ is H.

According to one embodiment, there is provided a compound of formula (I), wherein X and L together with their attached positions can be forming a substituted or unsubstituted heterocyclyl.

According to one embodiment, there is provided a compound of formula (I), wherein Ra is H, substituted or unsubstituted alkyl, C(O)$_2$R', —C$_3$H$_6$SCH$_3$, substituted or unsubstituted phenyl, substituted or unsubstituted benzyl, and substituted or unsubstituted heterocyclyl.

According to one embodiment, there is provided a compound of formula (I), wherein n is 3.

According to one embodiment, there is provided a compound of formula (I), wherein R' and R" are independently selected from H, $CH_3$, and 4-allyl-6-methoxyphenyl.

According to one embodiment, there is provided, a combination of formula (II), a pharmaceutical composition of formula (II)

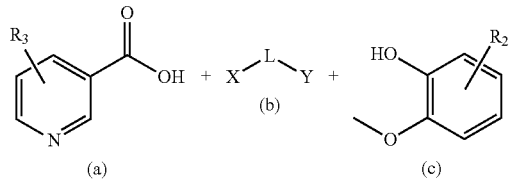

(II)

which comprises all the three components (a), (b), (c) like pyridine carboxylic acid, X-L-Y and methoxy benzene derivative, wherein X and Y represent H or groups defined above for formula (I) and use in treating Alzheimer's disease.

According to one more embodiment, there is provided a combination of formula (III), a pharmaceutical composition of formula (III),

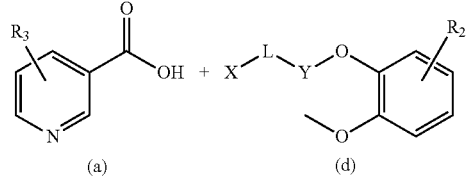

(III)

which comprises the two components of the formula (III), wherein the two components (a) and (d) are like pyridine carboxylic acid, methoxy benzene derivative; wherein X and Y represent H or groups defined above for formula (I) and their use in treating Alzheimer's disease dementia and other neurodegenerative diseases such as ischemic stroke, Parkinson's disease.

According to one more embodiment, there is provided a combination of formula (IV), a pharmaceutical composition of formula (IV)

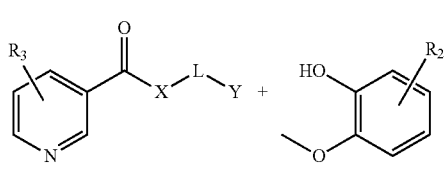

(IV)

which comprises two components like pyridine carboxylic acid derivative, methoxy benzene derivative, where in X and Y represent H or groups defined above for formula (I) which comprises two components of the formula (IV), and their use in treating Alzheimer's disease, dementia and other neurodegenerative diseases.

In a preferred embodiment. compounds of present invention are represented by

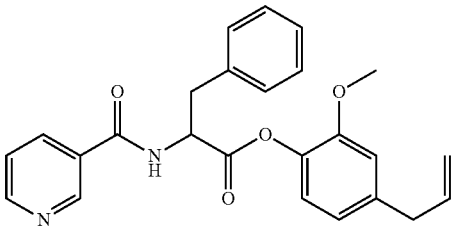 [SMILES: C=CCc1ccc(OC(=O)C(Cc2ccccc2)NC(=O)c2cccnc2)c(OC)c1]

1

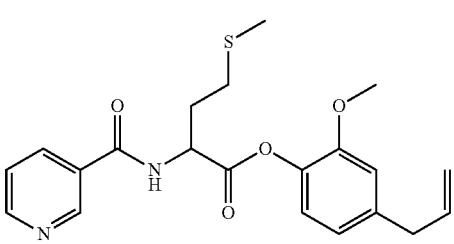 [SMILES: C=CCc1ccc(OC(=O)C(CCSC)NC(=O)c2cccnc2)c(OC)c1]

2

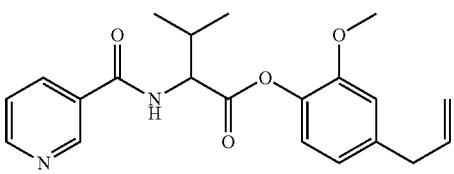

3

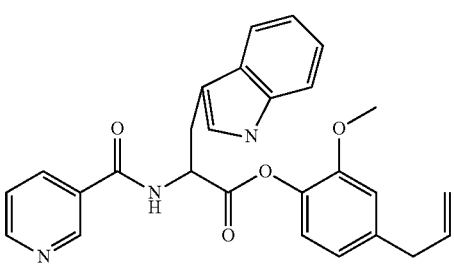

4

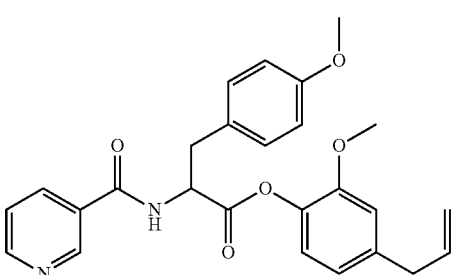

5

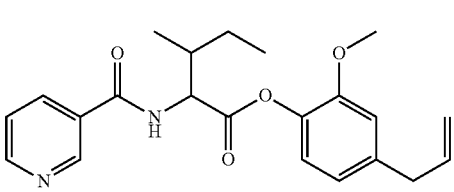

6

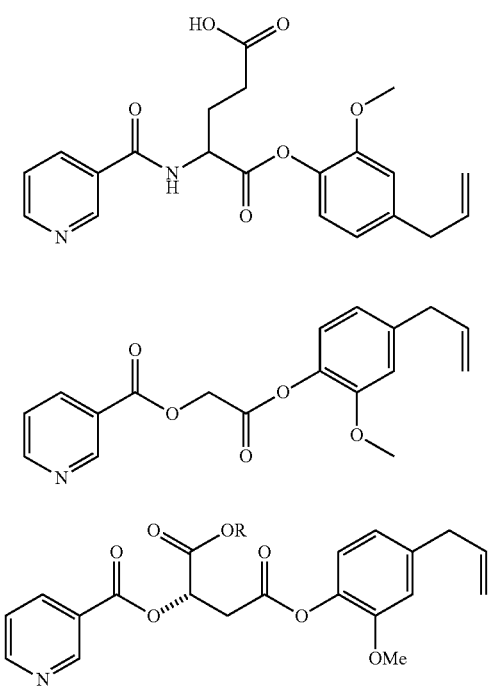

R = CH3    Compound 9
R = CH2CH3    Compound 16

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched chain having from 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkanoyl group" is used to denote a linear or branched aliphatic acyl group (preferably a C2-6 alkanoyl group) or an aromatic acyl group, which contains 2 to 10 carbon atoms. Examples include an acetyl group, a propionyl group, a pivaloyl group, a butyryl group, an isobutyryl group, a valeryl group and a benzoyl group, with an acetyl group being preferred.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups and spirobicyclic groups, e.g., spiro (4,4) non-2-yl.

The term "aryl" refers to an aromatic radical having from 6 to 14 carbon atoms such as phenyl, naphthyl, tetrahydronapthyl, indanyl, and biphenyl.

The term "arylalkyl" refers to an aryl group as defined above directly bonded to an alkyl group as defined above, e.g., —CH2C6H5 and —CH2CH2C6H5. "Substituted" refers to 1-3 substituents on the same position or on different positions with the same groups or different groups.

"Alkynyl" refers to alkynyl groups having from 2 to 6 carbon atoms and having at least one alkynyl saturation, example for such group includes acetylenyl, propargyl.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl)

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, COORx, —C(O)Rx, —C(S)Rx, —C(O)NRxRy, —C(O)ONRxRy, —NRxCONRyRz, —N(Rx)SORy, —N(Rx)SO2Ry, —(=N—N(Rx)Ry), —NRxC(O)ORy, —NRxRy, —NRxC(O)Ry, —NRxC(S)Ry, —NRxC(S)NRyRz, —SONRxRy, —SO2NRxRy, —ORx, —ORxC(O)NRyRz, —ORxC(O) ORy, —OC(O)Rx, —OC(O)NRxRy, —RxNRyC(O)Rz, —RxORy, —RxC(O)ORy, —RxC(O)NRyRz, —RxC(O) Ry, —RxOC(O)Ry, —SRx, —SORx, —SO2Rx, and —ONO2, wherein Rx, Ry and Rz are independently selected from hydrogen, substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The terms "halogen" or "halo" includes fluorine, chlorine, bromine, or iodine.

The term "haloalkyl" is used to denote a group comprised of an alkyl group substituted with halogen atom, where alkyl group is as defined above and halogen is used to denote fluorine, chlorine, bromine or iodine, an example of such group is trifluoromethyl, difluoromethyl.

The term "alkoxy group" is used to denote a linear or branched alkoxy group containing 1 to 6 carbon atoms. Preferred are C1-4 alkoxy groups including a methoxy group, an ethoxy group, a propoxy group, an isopropoxy group, an n-butoxy group, an isobutoxy group and a tert-butoxy group.

The term "alkoxycarbonyl group" issued to denote a structure composed of a linear or branched C1-5 alkoxy group and a carbonyl group. Preferred are C2-5 alkoxycarbonyl groups including a methoxycarbonyl group, an ethoxycarbonyl group, a propoxycarbonyl group, an isopropoxycarbonyl group and a butoxycarbonyl group. Among them, a methoxycarbonyl group is preferred.

The term "prodrug" means a compound that is transformed in vivo to yield a compound of Formula (I) (II) or (IIA) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms or (4) lessening the severity of a state, disease, disorder or condition or at least one clinical or subclinical symptom thereof.

The compounds described in the present invention may form salts. Non-limiting examples of pharmaceutically acceptable salts forming part of this patent application include salts derived from inorganic bases salts of organic bases salts of chiral bases, salts of natural amino acids and salts of non-natural amino acids. Certain compounds of present patent application are capable of existing in stereoisomeric forms (e.g. diastereomers and enantiomers). With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutically acceptable solvates include hydrates, polymorphs, crystal forms and other solvents of crystallization (such as alcohols). The compounds of the present invention may form solvates with low molecular weight solvents by methods known in the art.

Pharmaceutical Compositions

The pharmaceutical compositions provided in the present patent application include at least one compound described herein and at least one pharmaceutically acceptable excipient (such as a pharmaceutically acceptable carrier or diluent). Preferably, the contemplated pharmaceutical compositions include a compound(s) described herein in an amount sufficient to treat AD, dementia or other neurodegenerative diseases.

The subjects contemplated include, for example, a living cell and a mammal, including human being. The compound(s) of the present invention may be associated with a pharmaceutically acceptable excipient (such as a carrier or a diluent) or be diluted by a carrier, or enclosed within a carrier which can be in the form of a capsule, tablet, powder, syrup, patch.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared, e.g., as described in Remington: The Science and Practice of Pharmacy, 20th Ed., 2003 (Lippincott Williams & Wilkins). For example, the active compound can be mixed with a carrier, or diluted by a carrier. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be, for example, capsules, tablets, aerosols, solutions, suspensions or injectible forms The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (Aerosil®), 1.5 mounds microcrystalline cellulose (Avicel®), 70 mg modified cellulose gum (Ac-Di-Sol®), and 7.5 mg magnesium stearate; (2) Coating: HPMC, approx. 9 mg Mywacett 9-40 T and approx. 0.9 mg acylated monoglyceride. Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention provides a method for treating or lessening the severity of disorder associated with amyloid-beta-42 peptide, wherein said method comprises administering to said subject a compound of formula(I) there of. Such disorders include Alzheimer's disease, dementia and other neurodegenerative disorders such as such as ischemic stroke, Parkinson's disease Methods of Preparation The compounds described herein may be prepared by techniques known in the art. In addition, the compounds described herein may be prepared by following the reaction sequence as depicted in Scheme-1 to 2. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereo isomers of the compounds in these schemes, unless otherwise specified, are also encompassed within the scope of this invention.

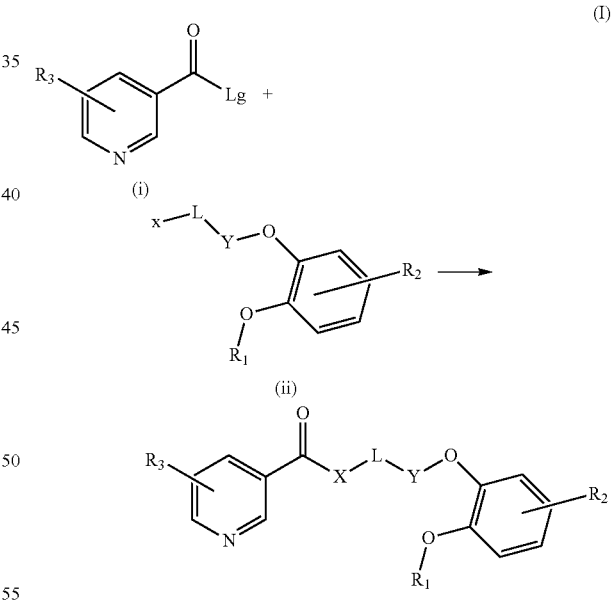

Compound of formula (i) where in Lg is a leaving group, can be reacted with formula (ii) by the methods known in the art. For example when Lg is OH formula (i) can be coupled with formula (ii) in the presence of coupling agents such as DCC, N,N,N',N'-tetramethyl-o-(benzotriazol-1-yl)uronium tetrafluoroborate (TBTU), 1-Ethyl-3-(3-Dimethylaminopropyl)carbodiimide (EDCI), hydroxybenzotriazole (HOBt) or the like in the solvents such as for example, N-methyl morpholine (NMM), dimethylformamide, diiospropyl ethylamine, dichloromethane, ethyl acetate or the like to obtain compound of formula (I)

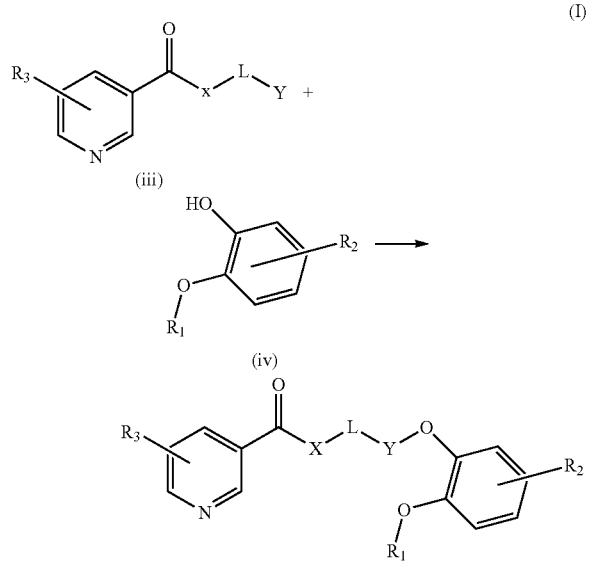

Similarly by following the method above, compound of formula I can be prepared by coupling formula (iii) with formula (iv).

Methods for In Vitro and In Vivo Experiments:

Human Neuronal Cell Model:

We used the human Neuroblastoma SH-SY5Y cells for drug testing as a model for Aβ42 production. The cells were cultured in Dulbecco's modified Eagle's medium or Dulbecco's modified Eagle's medium/Ham's F-12 medium supplemented with 10% fetal bovine serum, 100 units/ml penicillin, and 100 μg/ml streptomycin in a humidified atmosphere of 95% air, 5% CO2 at 37° C. as per suppliers instructions. Cells were typically incubated with the compounds overnight and then, media was harvested for Aβ42 quantitation as described below. Cell toxicity was monitored using the MTT assay and all data reported are corrected for any cell loss.

Sandwich Enzyme-Linked Immunosorbent Assay (sELISA) for Quantization of Aβ42:

The capture antibody, detection antibody and secondary antibody as well as standard purified preparations of Aβ42 were obtained from Sigma-Aldrich. Cells were cultured for 24 h in the presence or absence of compounds and the conditioned medium was subjected to sELISA.

Testing of Compound 9 on Scopolamine Induced Memory Deficit in Novel Object Recognition Task in Wistar Rats:

The effect of drugs tested in a rat cognition model often used to test improvements in cognition, namely the scopolamine induced memory deficit in novel object recognition task (Ennaceur A, Delacour J. A new one-trial test for neurobiological studies of memory in rats. 1: Behavioral data. Behav Brain Res. 1988; 31:47-59). Male rats are administered with vehicle or test compounds (donezepil at or compound at 0, 1, 3, 10, 30 or 100 mg/kg body weight) for 7 days before the initiation of habituation and continued through out the novel object recognition task experimentation period.

The test will be conducted as follows: On day 1 the rats will be acclimatized for 20 min to their respective arenas (one hour after administering with vehicle or test compounds) and then returned to their respective home cages. On day 2 the rats will be administered vehicle or test compound one hour prior to trial. Donpezil will be administered once, 30 minutes prior to familiarization phase. Scopolamine (1 mg/kg, i.p.) will be injected 20 min prior to trial. 20 min after scopolamine administration, rats will be subjected to familiarization phase. Handling will be done by individually placing the animals on the palm of the hand for 10 to 15 sec before placing it into arena. During the familiarization phase rats will be allowed to explore for 3 min the arenas containing two similar objects (familiar objects, plastic bottles, 12 cm high×5 cm diameter) covered with yellow masking tape. The time spent investigating each of the identical objects will be recorded by an investigator (blind to the treatment) using hand held stopwatches. All the trials will be video recorded. Investigation of the objects is defined as smelling, sniffing, licking, nose within 1 cm radius of the object with moving vibrissae, touching the object with fore paw having nose directed towards the object. After the trial is completed animals will be returned to their home cages. After an inter trial interval of 3 min the rats will be subjected to choice trial for a period of 3 min. Here the rats will be allowed to explore the arena, which contains a copy of the familiar object and a novel object (amber color glass bottle, 11.5 cm high×4.5 cm diameter). The time spent investigating the novel and familiar objects will be recorded by the same investigator (investigator who scored familiarization phase and blind to the treatment) using hand held stopwatches. Exploration of each animal will be recorded on the DVD recorder using a camera held above the arena. Animals, which show the exploration of greater than or equal to 15 sec during the familiarization trial and 10 sec during the choice trail, will be considered in the data analysis. This is to ensure that the animals received object training. The animal that shows selective exploration (defined as exploration of one object 20 seconds more than the other object in familiarization phase) will not be considered for data analysis. The novel object recognition task experimentation will be carried out over a period of 4 days i.e. first 6 animals will be experimented on first two days and the next 6 animals will be experimented on next 2 days (The 7 day dosing schedule will be initiated accordingly such that all animals receive 7 doses of vehicle or test drug before the day of habituation. Totally each animal would receive 9 doses of vehicle or test drug). Statistical analysis: For each treatment group, the time spent with the novel and familiar objects will be compared by Student's paired 't'test. The discriminative index for the drug treated groups will be compared to that of the vehicle group by use of the Kruskal-Wallis test. The discriminative index is ratio of time spent exploring the novel object divided by sum of time spent exploring the novel object and familiar object in choice trial. Outliers based on discriminative index (Grubbs outlier test (or) greater or less than two standard deviation from mean) will not be considered for statistical analysis.

Testing the Effect of Compound 9 on Brain Abeta-42 Levels in Rat Model:

Drug Treatment

Animals are randomized into different treatment groups based on body weight. The test compounds are administered orally for 2 weeks while the control animals are administered the vehicle alone.

Brain Tissue Preparation

At the end of the study, animals are sacrificed 2 hours after the last dose and brain samples are excised and immediately frozen on dry ice. The frozen brains are homogenized in 3 volumes (w/v) of ice-cold 0.2% Diethylamine containing 50 mM NaCl, pH 10, and protease inhibitors, and then centrifuged at 15000 rpm at 4° C. for 30 min using a centrifuge.

The resulting supernatant is retained as the soluble fraction and neutralized by addition of 10% 0.5 M Tris-HCl, pH 6.8.

Determination of Aβ-42 Levels

Aβ levels in plasma, CSF and brain tissue extracts are determined by ELISA using Anti-Ab42 antibody from Sigma (Anti-Amyloid Peptide β, Cleavage Site 42, A 1976).

ELISA Protocol

Ar3-42 levels in brain tissue extracts were determined by ELISA. Monoclonal anti β-Amyloid Clone BAM-10 monoclonal antibody (Sigma, A3981) was diluted 1:1000 with coating buffer to get a working concentration of 1.5 μg/μL. 100 μL of this was coated per well in a 96 well immunoplate (NUNC) at 4° C. for 16-18 hours. The plate was washed 3× with 230 μL of wash buffer. The wells were then blocked with 150 μL of blocking buffer for 1 hour. The plate was washed 3× with 230 μL of wash buffer. Samples, standard (2500-1.1 ng/ml) and blank were added to the appropriate wells and incubated with mild shaking for 2 hours. The plate was then washed 3× with 230 μL of wash buffer. The secondary antibody (anti-Amyloid peptide, cleavage site 42, Sigma A1976) was diluted 1:1000 with 1% BSA to get a working concentration of 1.25 μg/μL). 100 μL of this was added per well and incubated with mild shaking for 2 hours. The plate was washed 3× with 230 μl of wash buffer. 100 lit of Detection antibody, Anti-rabbit IgG whole molecule HRP conjugate (Sigma A6154 diluted 1:1000 with 1% BSA) added in to the wells and incubated for 2 hours with mild shaking. The plate was washed 3× with 230 μl of wash buffer followed by 100 μL of Strepavidin HRP (1:200 diluted with 1% BSA). The plate was 3× with 230 μL of wash buffer and 100 μL of TMB/$H_2O_2$ substrate was added and incubated for 20 minutes. The reaction was topped by adding 50 μL of 2N $H_2SO_4$ and the absorbance was measured at 450/570 nm in a microplate reader (BioTek)

Effect of Compound 9 on Memory Deficit in Morris Water Maze Task in Wistar Rats:

The Morris Water Maze is a commonly used test for cognitive measurements (D'Hooge R, De Deyn P P. Applications of the Morris water maze in the study of learning and memory. Brain Res Brain Res Rev. 2001; 36:60-90). Male wistar rats are used for this study. The Water maze consists of a 1.8 m diameter; 0.6 m high circular tank filled with water (24±2° C.). A platform 16 cm diameter will be placed 1.0 cm below the water surface in the center of one of the four imaginary quadrants, which remains constant for all the rats. COMPOUND 9 was administered for 5 days prior to acquisition trial and continued throughout the acquisition trials. During the acquisition trails COMPOUND 9 was administered 60 min prior to the trail. Donepezil was administered 50 minutes acquisition trials. Scopolamine was administered 30 minutes acquisition trials. Rats were lowered gently, feet first into water. A rat was allowed to swim for 60 s to find the platform. If the platform was found during this time the trial was stopped and rat was allowed to stay on platform for 30 s before being removed from the maze. If the platform was not found during 60 s trial, then the rat was manually placed on the platform facing a visual cue and allowed to stay on platform for 30 s before being removed from the maze. The rats were taken off the platform (ensuring that the rat sees the investigator's hand from the front before removal) and dried with a towel gently. Each rat received 4 trials in a day. The maze has 8 starting points. On the first and third day the animals started from $1^{st}$, $3^{rd}$, $5^{th}$ & $7^{th}$ starting points. On the second and fourth day the animals started from $2^{nd}$, $4^{th}$, $6^{th}$ & $7^{th}$ starting points. Retention of the task was assessed on $5^{th}$ day in which each animal received a single 120 s probe trial during which platform was removed from the pool. Rats were not treated prior to retention trail. Rats were placed under a heating lamp for 5 min before being returned to its home cage. Latency to reach the platform (ms), swim speed (cm/s) and path length (cm) was measured in acquisition trials. Percentage time spent in target quadrant (quadrant in which platform is placed during acquisition training) and swim speed (cm/s) was calculated in probe trial. The animals were tracked and the data was generated using the Video Mot 2 software.

Experimentation was carried out over a period of 10 days i.e. first 6 animals was experimented on first five days and the next 6 animals was experimented on next five days (Pretreatment and testing schedule was initiated accordingly such that all animals receive 9 doses of vehicle or test drug). Data obtained was analyzed by Repeated measures Two way ANOVA followed by Bonferroni post tests by using the Graph pad prism software package.

Effect of Compound 9 in Transgenic Model of Alzheimer's Disease Tg2576 Mice

The study used 6-month old Tg (HuApp695.K670-M671L) 2576 transgenic and age-matched C57B16/SJL non-transgenic control mice (Hsiao K, Chapman P, Nilsen S, Eckman C, Harigaya Y, et al. Correlative memory deficits, Abeta elevation, and amyloid plaques in transgenic mice. Science. 1996; 274:99-102). Mice were obtained from Jackson Labs and a colony was established. Tg2576 transgenic mice over-express human APP with the double Swedish mutation. Tg2756 and control mice were treated for a period of 4 weeks with either 1) vehicle alone n=10), 2) compound 9 (50 mg/kg dosed orally; n=10). Soluble brain aβ-42 and aβ-40 were measured using the typical ELISA protocol described before.

EXAMPLES

Example 1

Preparation of 3-phenyl-2-[(pyridine-3-carbonyl)-amino]-propionic acid-4-allyl2-methoxy-phenylester

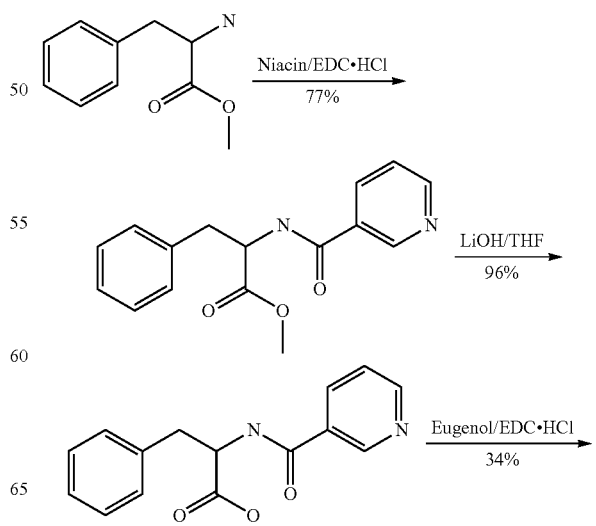

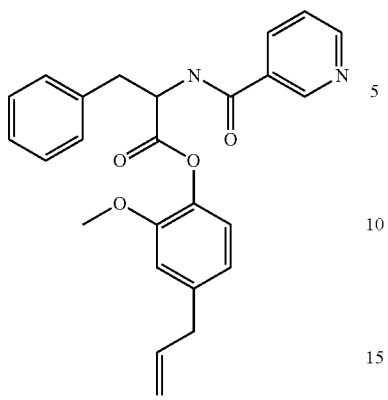

Step 1: Preparation of 3-phenyl-2-[(pyridine-3-carbonyl)-amino]-propionic acid methylester

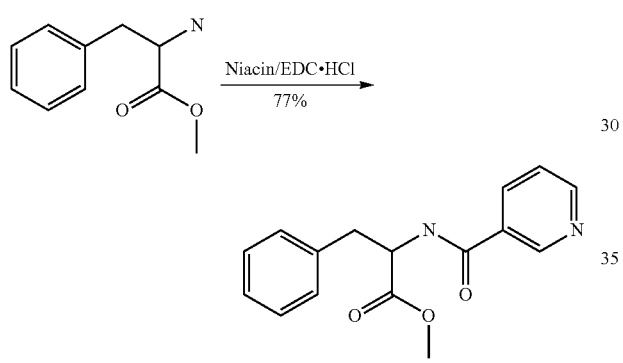

To a solution of nicotinic acid (1.64 g, 1.11 mmol), in DCM (20 mL) were added EDCI.HCl (4.2 g, 2.22 mmol), N-methyl morpholine (3.6 mL, 3.33 mmol) and phenylalaninemethylester (2.0 g, 1.11 mmol). The mixture was allowed to stir at room temperature (25° C.) overnight under nitrogen. The resulting mixture was diluted with DCM (200 mL), washed with water (2×100 mL) and dried over sodium sulphate. The crude product obtained upon evaporation of the solvent was further purified by silica gel column chromatography to obtain product as off-white solid.

Step 2: Preparation of 3-phenyl-2-[(pyridine-3-carbonyl)-amino]-propionic acid

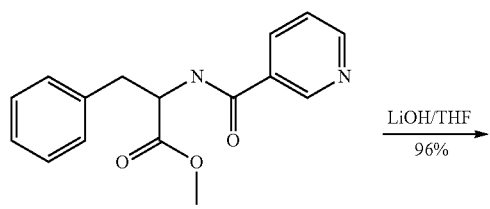

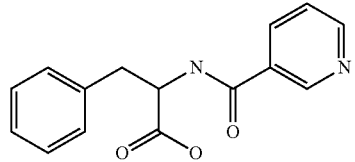

To a solution of 3-phenyl-2-[(pyridine-3-carbonyl)-amino]-propionic acid methylester (1.2 g, 4.2 mmol) in methanol (10 mL), THF (30 mL) was added LiOH (0.885 g, 21.1 mmol) dissolved in water (10 mL). The mixture was allowed to stir at room temperature (25° C.) over a period of 2 hrs. THF was evaporated from reaction mixture, acidified with 1.5N HCl then extracted with ethylacetate (200 mL) and concentrated to obtain product as yellow color solid (1.0 g, 96%).

Step 3: Preparation of 3-phenyl-2-[(pyridine-3-carbonyl)-amino]-propionic acid-4-allyl2-methoxy-phenylester

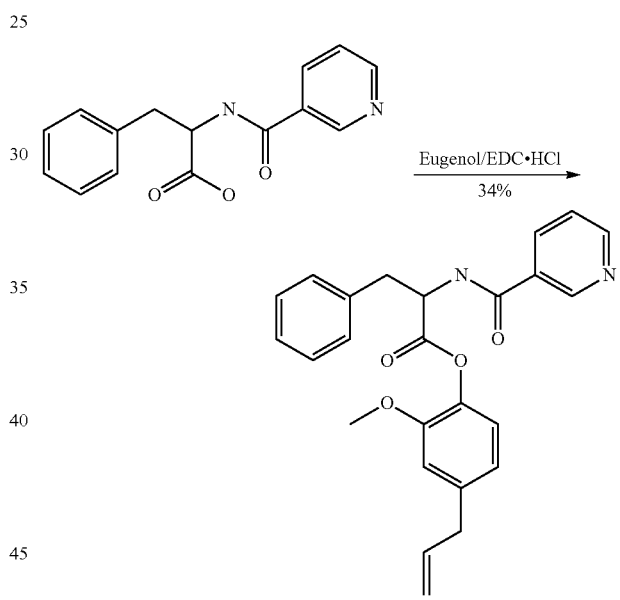

To a solution of 3-phenyl-2-[(pyridine-3-carbonyl)-amino]-propionic acid (0.350 g, 1.2 mmol), in DCM (3 mL) were added EDC.HCl (0.450 g, 2.4 mmol), N-methyl morpholine (0.4 mL, 3.6 mmol), Eugenol (0.23 mL, 0.0015 mmol). The mixture was allowed to stir at room temperature (25° C.) overnight under nitrogen. The resulting mixture was diluted with ethyl acetate (100 mL), washed with water (3×50 mL) and dried over sodium sulphate. The crude product obtained upon evaporation of the solvent was further purified by silica gel column chromatography to obtain required product as off-white solid (0.170 g, 34%).

$^1$H NMR (300 MHz, CDCl$_3$) δ (ppm): 3.18-3.43 (m, 4H), 3.74 (s, 3H), 4.92-5.13 (bs, 1H), 6.76-6.78 (m, 1H), 6.97-7.00 (m, 2H), 7.19-7.53 (m, 6H), 8.15 (d, J=7.8 Hz, 1H), 8.71 (d, J=4.5 Hz, 1H), 8.95 (s, 1H), 9.24 (m, 1H).

LCMS (ESI) m/z: 416.9 ([M+H]$^+$).

HPLC purity: 97.72%

Nature of the compound: off-white solid

Example 2

Preparation of 4-methyl-sulfanyl-2-[(pyridine-3carbonyl)-amino] butyric acid-4-allyl-2-methoxy phenyl ester

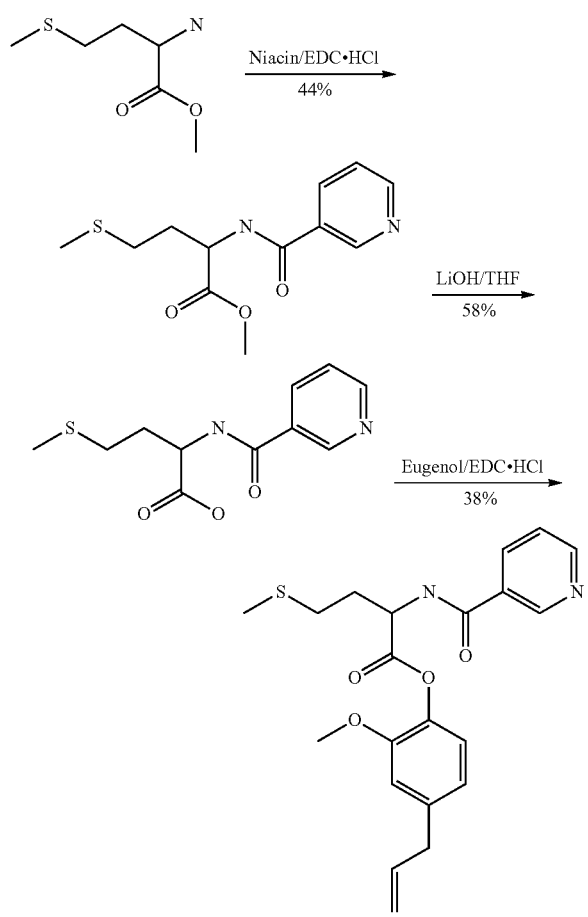

Step 1: Preparation of 4-methyl-sulfanyl-2-[(pyridine-3carbonyl)-amino] butyric acid methylester

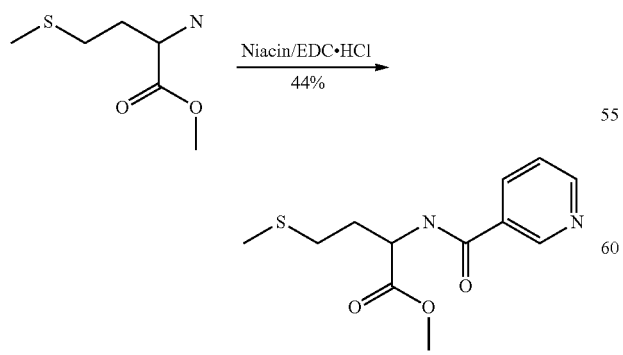

To a solution of nicotinic acid (1.8 g, 14.7 mmol), in DCM (20 mL) were added EDCI.HCl (4.7 g, 24.6 mmol), N-methyl morpholine (6.7 mL, 61.5 mmol) and methionine ester (2.0 g, 12.3 mmol) under nitrogen. The mixture was allowed to stir at room temperature (25° C.) over 2 h under nitrogen. The resulting mixture was diluted with ethylacetate (200 mL), washed with water (2×100 mL) and dried over sodium sulphate. The crude product obtained upon evaporation of the solvent was further purified by silica gel column chromatography to obtain product as yellow colour solid (1.45 g, 44%)

Step 2: Preparation of 4-methyl-sulfanyl-2-[(pyridine-3carbonyl)-amino] butyric acid

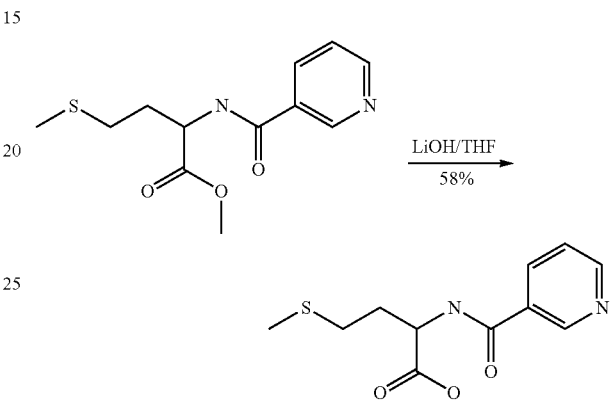

To a solution of ester (0.5 g, 1.54 mmol) in methanol (5 mL), THF (6 mL) was added LiOH (0.32 g, 7.73 mmol) dissolved in water (3 mL). The mixture was allowed to stir at room temperature (25° C.) over 2 h. solvent was evaporated, diluted with water (10 mL) acidified with 1.5N HCl, extracted with ethylacetate (100 mL), dried over sodium sulphate and concentrated to obtain yellow colour solid (0.23 g, 58%).

Step 3: Preparation of 4-methyl-sulfanyl-2-[(pyridine-3carbonyl)-amino] butyric acid-4-allyl-2-methoxy phenyl ester

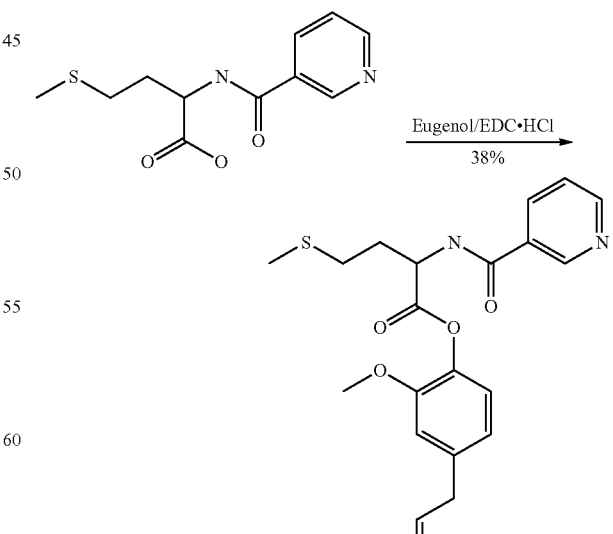

To a solution of compound 4-methyl-sulfanyl-2-[(pyridine-3carbonyl)-amino] butyric acid (0.25 g, 0.98 mmol), in DCM (3 mL), were added N-methylmorpholine (0.21 g, 1.96 mmol), EDCI.HCl (0.56 g, 0.29 mmol) and eugenol (0.15 mL, 0.98 mmol). The mixture was allowed to stir at room temperature (25° C.) overnight under nitrogen. The resulting mixture was diluted with DCM (100 mL), washed with water (3×50 mL) and dried over sodium sulphate. The crude product obtained upon evaporation of the solvent was further purified by silica gel column chromatography to obtain required product as white solid (0.15 g, 38%).

$^1$H NMR (300 MHz, CDCl$_3$) δ (ppm): 2.17 (s, 3H), 2.46-2.52 (m, 2H), 2.80-2.84 (m, 2H), 3.38 (d, J=6.4 Hz, 2H), 5.08-5.28 (m, 3H), 5.89-6.02 (m, 1H), 6.76-6.78 (m, 2H), 7.00-7.05 (m, 1H), 7.71-7.59 (m, 1H), 8.60-8.82 (m, 3H), 9.69 (bs, 1H).

LCMS (ESI) nth: 400.9 ([M+H]$^+$).

HPLC purity: 91.41%

Nature of the compound: white solid

Example-3

Preparation of 3-methyl-2-[pyridine-3-carbonyl]-amino-butyric acid-4-allyl-2-methoxy phenyl ester

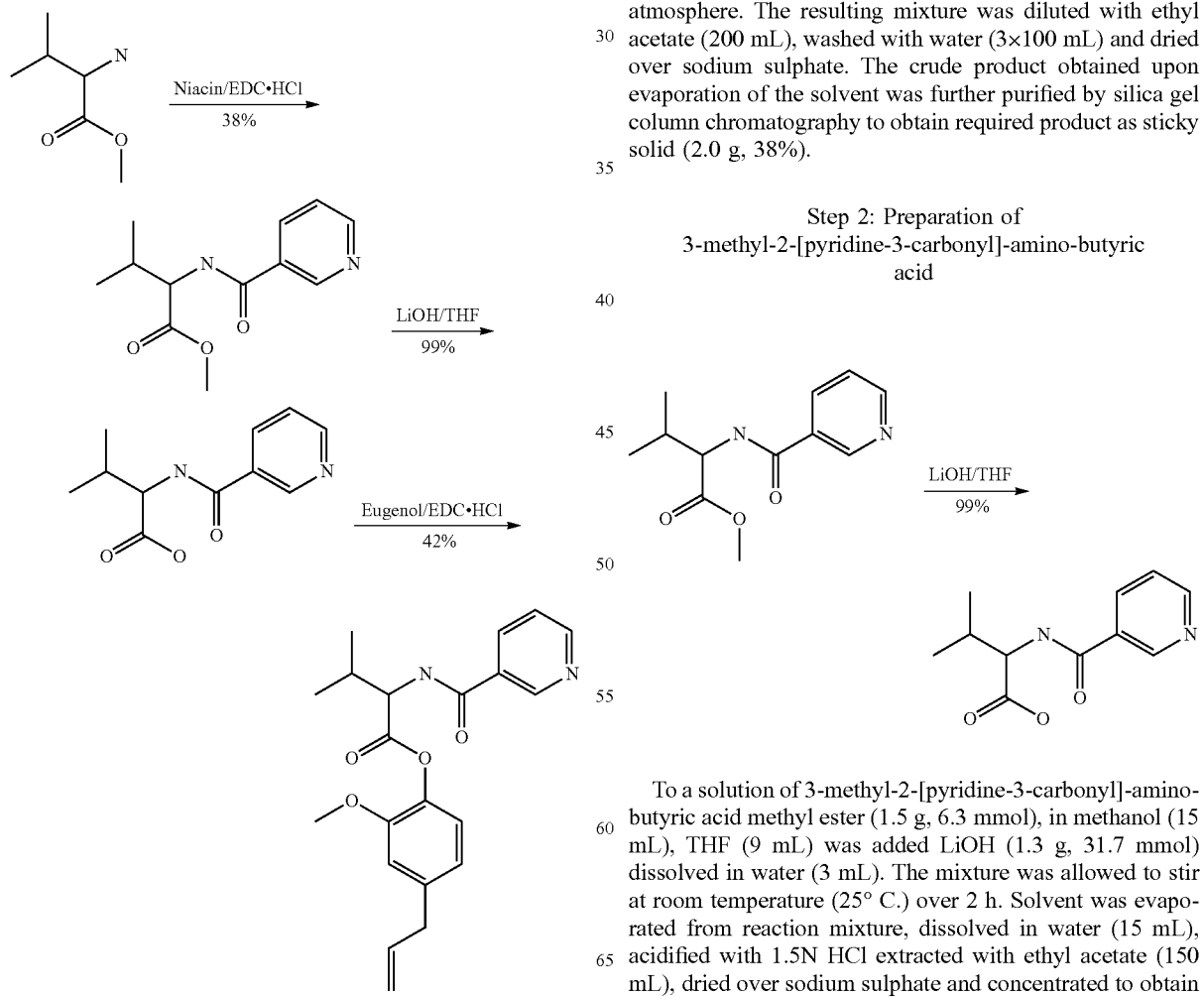

Step 1: Preparation of 3-methyl-2-[pyridine-3-carbonyl]-amino-butyric acid methyl ester

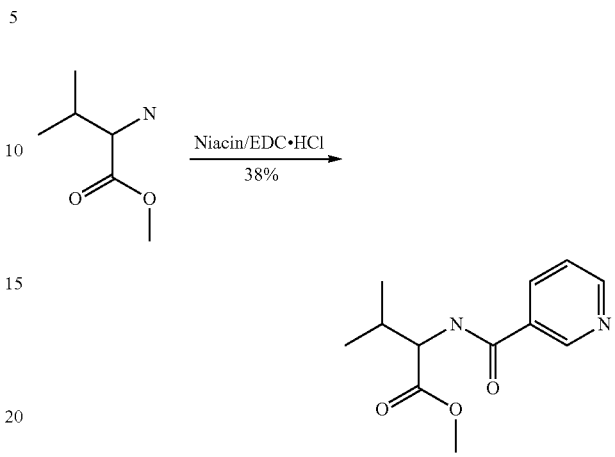

To a solution of L-valine methylester (3.0 g, 2.29 mmol), in DCM (30 mL) were added N-methyl morpholine (11.5 mL, 11.45 mmol), EDCI.HCl (8.7 g, 45.8 mmol) and nicotinic acid (3.3 g, 27.4 mmol). The mixture was allowed to stir at room temperature (25° C.) over 3 h under nitrogen atmosphere. The resulting mixture was diluted with ethyl acetate (200 mL), washed with water (3×100 mL) and dried over sodium sulphate. The crude product obtained upon evaporation of the solvent was further purified by silica gel column chromatography to obtain required product as sticky solid (2.0 g, 38%).

Step 2: Preparation of 3-methyl-2-[pyridine-3-carbonyl]-amino-butyric acid

To a solution of 3-methyl-2-[pyridine-3-carbonyl]-amino-butyric acid methyl ester (1.5 g, 6.3 mmol), in methanol (15 mL), THF (9 mL) was added LiOH (1.3 g, 31.7 mmol) dissolved in water (3 mL). The mixture was allowed to stir at room temperature (25° C.) over 2 h. Solvent was evaporated from reaction mixture, dissolved in water (15 mL), acidified with 1.5N HCl extracted with ethyl acetate (150 mL), dried over sodium sulphate and concentrated to obtain product as yellow colour solid (1.38 g, 99%).

Step 3: Preparation of 3-methyl-2-[pyridine-3-carbonyl]-amino-butyric acid-4-allyl-2-methoxy phenyl ester

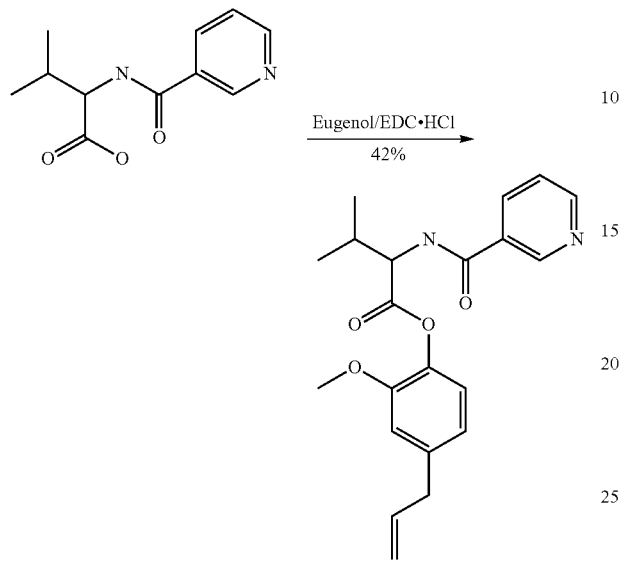

To a solution of preparation of 3-methyl-2-[pyridine-3-carbonyl]-amino-butyric acid (0.3 g, 1.35 mmol) in DCM (3 mL) were added N-methyl morpholine (0.44 mL, 4.0 mmol), EDCI.HCl (0.51 g, 2.7 mmol) and eugenol (0.24 mL, 1.62 mmol). The mixture was allowed to stir at room temperature (25° C.) overnight under nitrogen. The resulting mixture was diluted with DCM (100 mL), washed with water (3×50 mL) and dried over sodium sulphate. The crude product obtained upon evaporation of the solvent was further purified by silica gel column chromatography to obtain required product as white solid (0.20 g, 42%).

$^1$H NMR (300 MHz, DMSO-$d_6$) δ (ppm): 0.79-0.87 (m, 6H), 2.20-2.30 (m, 1H), 3.36 (m, 2H), 3.72 (s, 3H), 4.59-4.61 (bs, 1H), 5.04-5.14 (m, 2H), 5.96-5.98 (m, 1H), 6.75-6.78 (m, 1H), 6.95-7.00 (m, 2H), 7.51-7.56 (m, 1H), 8.23-8.25 (m, 1H), 8.72-8.74 (m, 1H), 8.97-9.05 (m, 2H).

LCMS (ESI) m/z: 369.0 ([M+H]$^+$).

HPLC purity: 92.86%

Nature of the compound: white solid

Example 4

Preparation of 3(1H-indol-3-yl)-2-[pyridine-3-carbonyl]-amino-propionic acid-5-allyl-2-methoxy phenylester

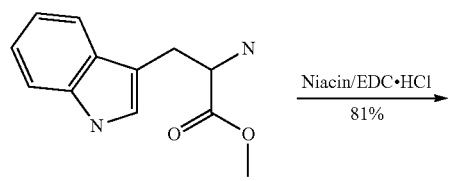

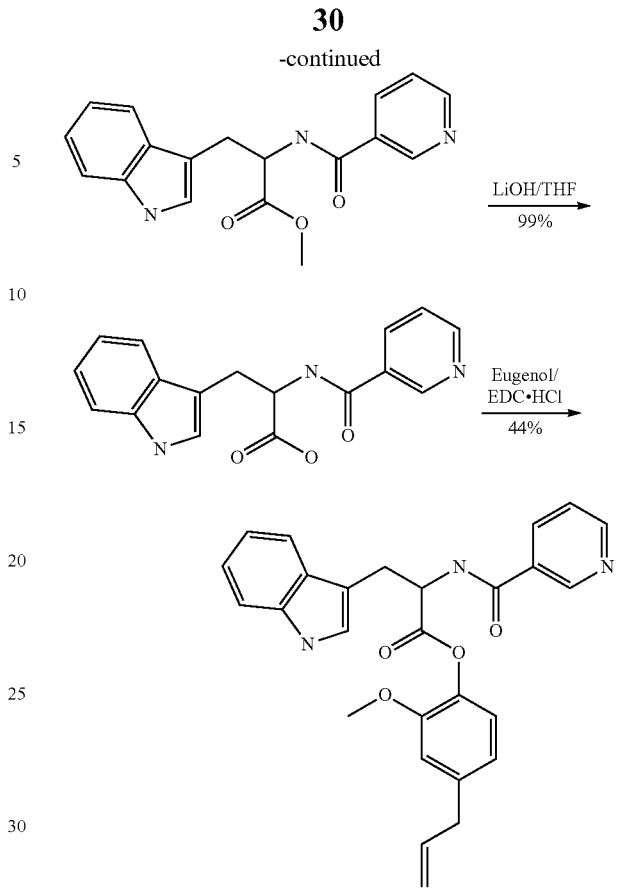

Step 1: Preparation of 3(1H-indol-3-yl)-2-[pyridine-3-carbonyl]-amino-propionic acid methylester

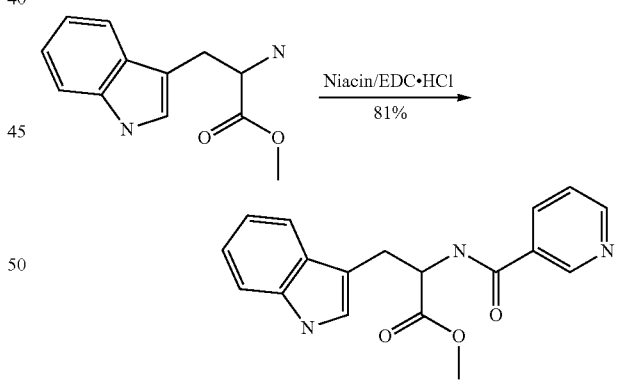

To a solution of methyl ester (2.0 g, 9.2 mmol), in DCM (20 mL) were added N-methyl morpholine (5 mL, 46.0 mmol), EDCI.HCl (3.5 g, 18.4 mmol) and nicotinic acid (2.0 g, 9.2 mmol). The mixture was allowed to stir at room temperature (25° C.) over 2 h under nitrogen atmosphere. The resulting mixture was diluted with ethylacetate (150 mL), washed with water (3×50 mL) and dried over sodium sulphate. The crude product obtained upon evaporation of the solvent was further purified by silica gel column chromatography to obtain required product as off-white solid (2.4 g, 81%).

Step 2: Preparation of 3(1H-indol-3-yl)-2-[pyridine-3-carbonyl]-amino-propionic acid

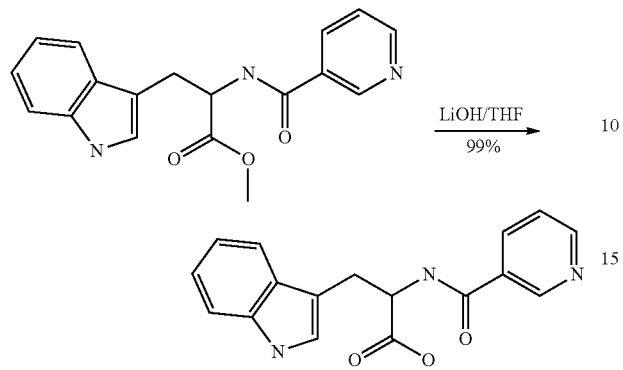

To a solution of 3(1H-indol-3-yl)-2-[pyridine-3-carbonyl]amino-propionic acid methylester (0.5 g, 1.6 mmol), in methanol (5 mL), THF (9 mL) was added LiOH (0.39 g, 7.70 mmol), dissolved in water (3 mL), The mixture was allowed to stir at room temperature (25° C.) over 2 h. Stripped off solvent, acidified reaction mass with 1.5N HCl, extracted with ethylacetate (100 mL) dried over sodium sulphate and concentrated to obtain product as colorless solid (0.48 g, 99%).

Step 3: Preparation of 3(1H-indol-3-yl)-2-[pyridine-3-carbonyl]-amino-propionic acid-5-allyl-2-methoxy phenylester To a solution of 3(1H-indol-3-yl)-2-[pyridine-3-carbonyl]-amino-propionic acid (0.23 g, 0.74 mmol) in DCM were added N-methyl morpholine (0.15 g, 1.44 mmol), EDCI.HCl (0.42 g, 2.2 mmol) and eugenol (0.12 g, 0.74 mmol). The mixture was allowed to stir at room temperature (25° C.) over 3 h under nitrogen atmosphere. The resulting mixture was diluted with DCM (50 mL), washed with water (3×50 mL) and dried over sodium sulphate. The crude product obtained upon evaporation of the solvent was further purified by silica gel column chromatography to obtain product as a yellow low melting solid (0.15 g, 44%).

$^1$H NMR (300 MHz, DMSO-$d_6$) δ (ppm): 3.37 (d, J=6.6 Hz, 2H), 3.40-3.49 (m, 1H), 3.74 (s, 3H), 5.05-5.14 (m, 3H), 5.90-6.01 (m, 1H), 6.75-6.78 (m, 1H), 6.94-7.07 (m, 4H), 7.32-7.36 (m, 2H), 7.56-7.64 (m, 2H), 8.22-8.32 (m, 1H), 8.74 (d, J=4.5 Hz, 1H), 9.01 (s, 1H), 9.29 (d, J=7.8 Hz, 1H), 10.91 (s, 1H).

LCMS (ESI) m/z: 455.8 ([M+H]$^+$).

HPLC purity: 99.58%

Nature of the compound: yellow low melting solid

Example 5

Preparation of 3-(4-hydroxy phenyl)2-[(pyridine-3-carbonyl)amino]propionic acid -4-allyl-2-methoxy phenyl ester

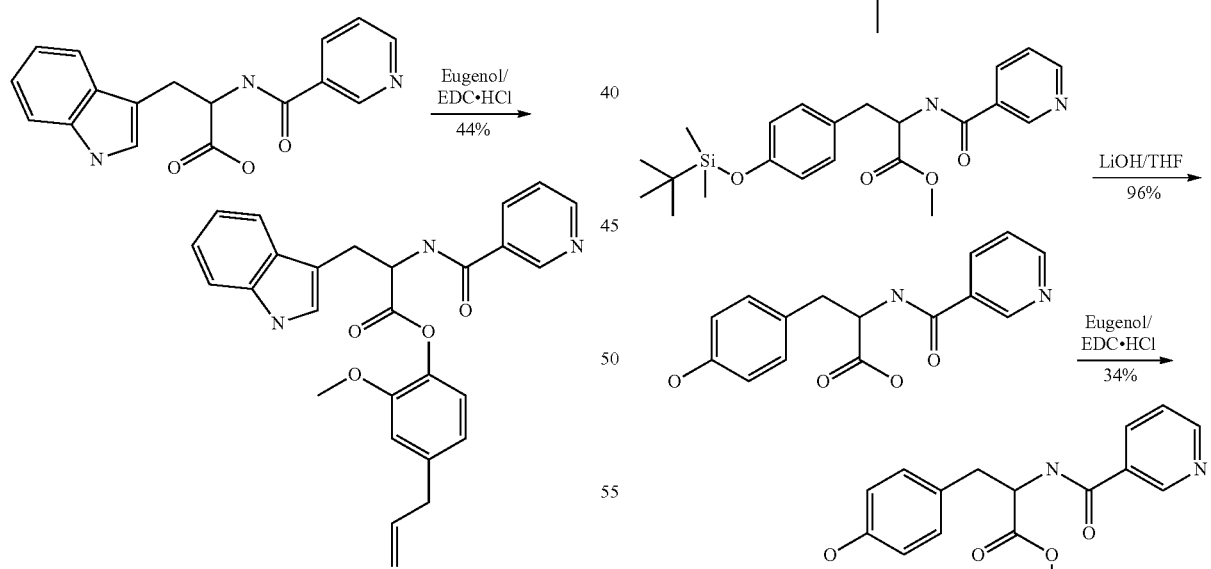

Step 1: Preparation of 3-(4-hydroxy phenyl) 2-[(pyridine-3-carbonyl)amino]propionic acid methyl ester

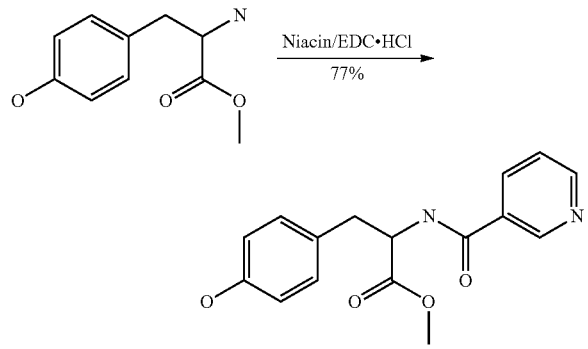

To a solution of niacin (1.26 g, 10.24 mmol), in DCM (20 mL), were added N-methyl morpholine (2.25 mL, 25.0 mmol), EDCI.HCl (5.87 g, 30.73 mmol) and amine (2.0 g, 10.24 mmol) under nitrogen. The mixture was allowed to stir at room temperature (25° C.) over 3 h under nitrogen atmosphere. The resulting mixture was diluted with DCM (200 mL), washed with water (3×100 mL) and dried over sodium sulphate. The crude product obtained upon evaporation of the solvent was further purified by silica gel column chromatography to obtain required product as white solid (1.7 g, 56.6%).

Step 2: Preparation of 3[4-(t-butyl-dimethyl-silyloxy) phenyl]2-[(pyridine-3-carbonyl)amino]propionic acid methyl ester To a solution of 3-(4-hydroxy phenyl) 2-[(pyridine-3-carbonyl)amino]propionic acid methyl ester (0.53 g, 1.76 mmol) in DMF (1 mL) was added N,N'-Di isopropyl ethyl amine (0.47 mL, 2.00 mmol) then reaction mixture cooled to (0° C.), t-butyl-dimethyl-silylchloride (0.26 g, 1.76 mmol), was added to reaction mass at (0° C.). The mixture was allowed to stir at room temperature (25° C.) over 5 h. The reaction mixture was quenched with ice, diluted with ethyl acetate (100 mL), washed with water (3×50 mL) and dried over sodium sulphate. The solvent was evaporated under reduced pressure to obtain product as pale brown liquid (0.6 g, 82%).

Step 3: Preparation of 3[4-(t-butyl-dimethyl-silyloxy) phenyl]2-[(pyridine-3-carbonyl)amino]propionic acid

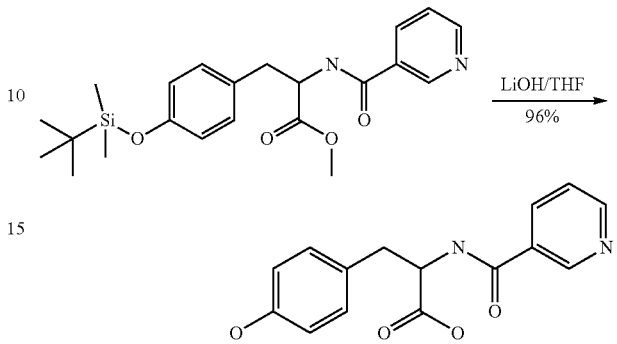

To a solution of methyl ester (0.91 g) in methanol (1 mL), THF (3 mL) was added LiOH (0.45 g, 10.97 mmol), dissolved in water (1 mL). The mixture was allowed to stir at room temperature (25° C.) over 3 h. Stripped off solvent from reaction mixture, acidified reaction mass using 1.5N HCl (pH=2-4). Free acid was extracted with ethyl acetate (200 mL), dried over sodium sulphate and concentrated. Obtained yellow colour solid was directly taken for next step.
Note: During this acid workup t-butyl dimethyl silylchloride cleavage was observed.

Step 4: Preparation of 3-(4-hydroxy phenyl)2-[(pyridine-3-carbonyl)amino]propionic acid -4-allyl-2-methoxy phenyl ester

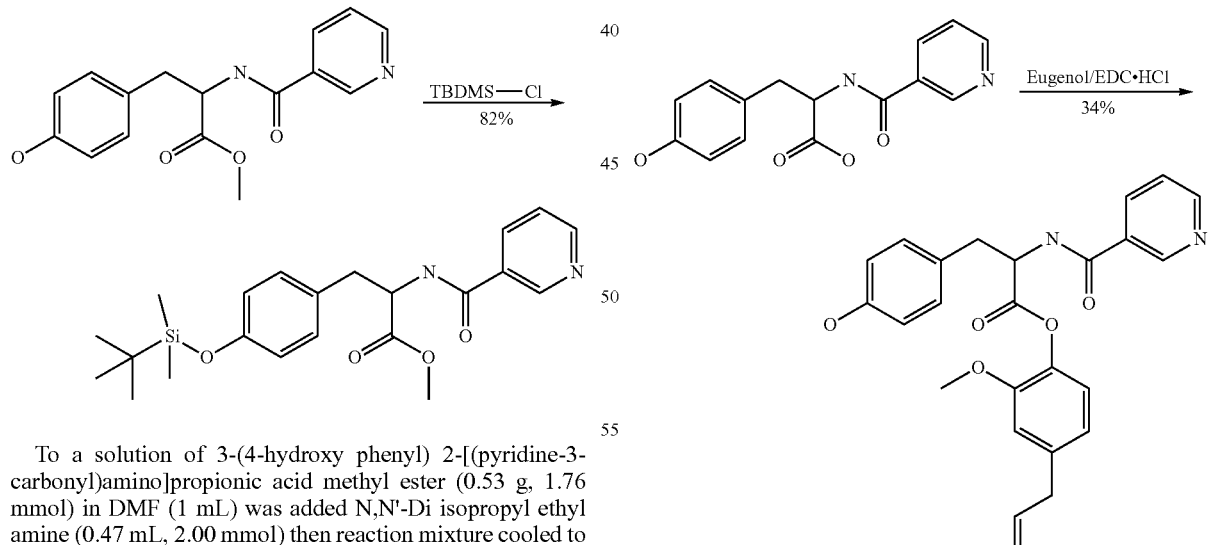

To a solution of 3[4-(t-butyl-dimethyl-silyloxy) phenyl] 2-[(pyridine-3-carbonyl)amino]propionic acid (0.498 g, 17.4 mmol) in DCM (40 mL) were added N-methyl morpholine (0.528 g, 5.2 mmol), EDCI.HCl (0.66 g, 3.4 mmol) and eugenol (0.22 g, 13.9 mmol). The mixture was allowed to stir at room temperature (25° C.) over 3 h under nitrogen atmosphere. The resulting mixture was diluted with DCM (100 mL), washed with water (3×50 mL) and dried over sodium sulphate. The crude product obtained upon evaporation of the solvent was further purified by silica gel column chromatography to obtain required product as pale yellow solid (0.75 g, 31.5%).

$^1$H NMR (300 MHz, DMSO-d$_6$) δ (ppm): 3.11-3.47 (m, 4H), 4.52 (s, 3H), 5.06-5.14 (m, 3H), 5.94-6.03 (m, 1H), 6.74-6.81 (m, 3H), 6.92-6.98 (m, 2H), 7.18-7.21 (m, 2H), 7.51-7.55 (m, 1H), 8.15-8.19 (m, 1H), 8.68 (d, J=3.9 Hz, 1H), 8.90 (bs, 1H).

LCMS (ESI) m/z: 433.1 ([M+H]$^+$).

HPLC purity: 99.5%

Nature of the compound: pale yellow solid

Example 6

Preparation of 3-methyl-2-[pyridine-3-carbonyl]-amino-pentanoic acid-4-allyl-2-methoxy phenyl ester Synthesis of KU-020

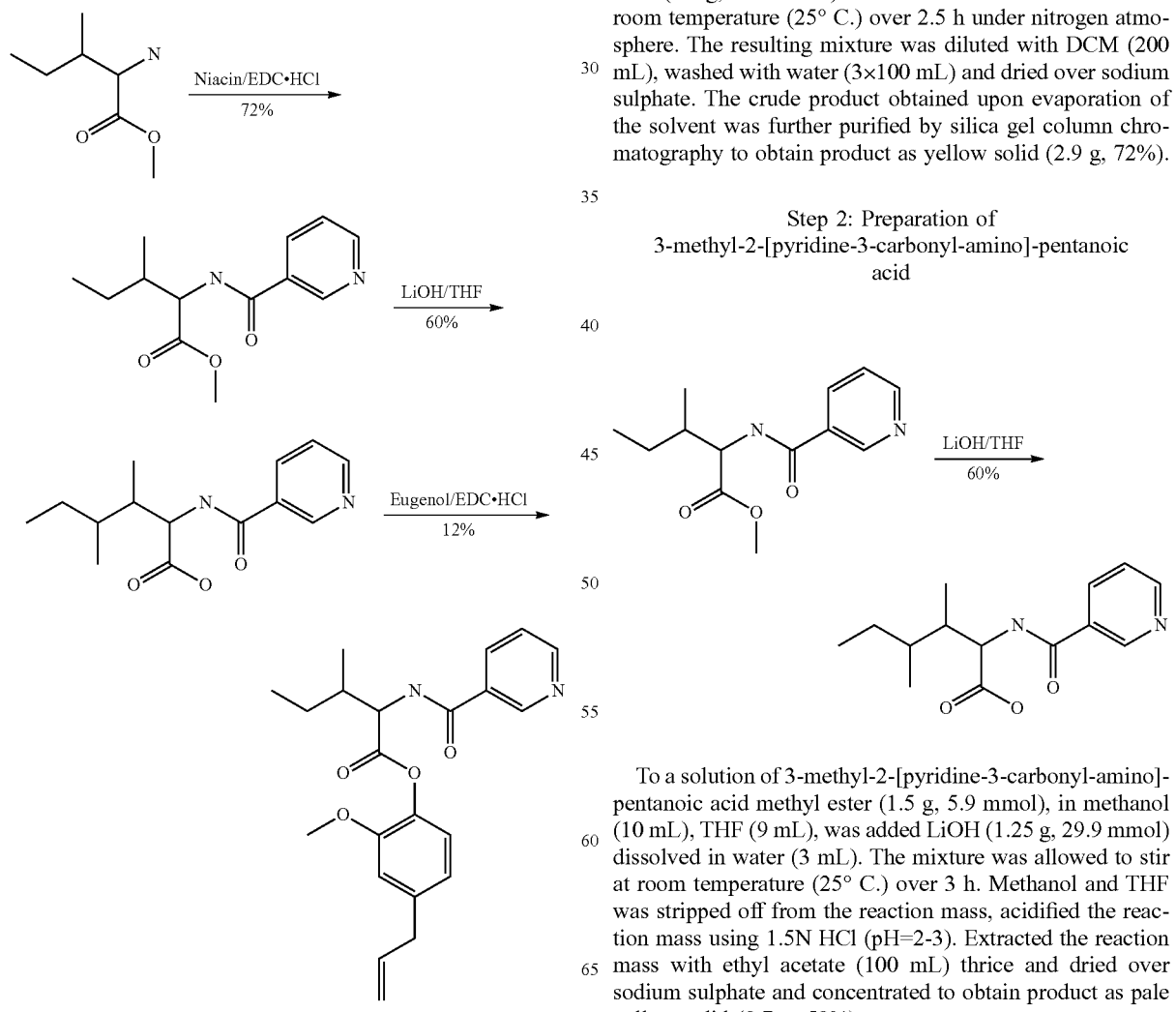

Step 1: Preparation of 3-methyl-2-[pyridine-3-carbonyl-amino]-pentanoic acid methyl ester

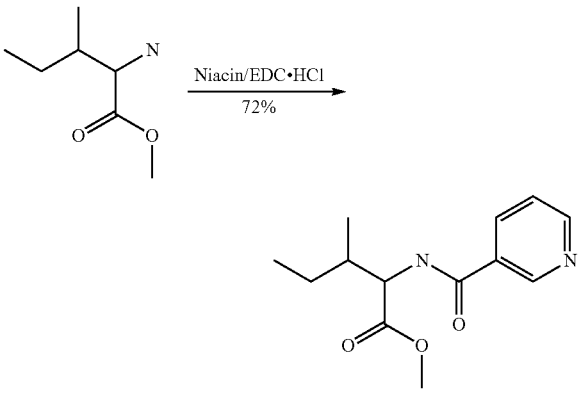

To a solution of nicotinic acid (2.0 g, 16.5 mmol) in DCM (20 mL), was added N-methylmorpholine (6.9 mL, 49.5 mmol), EDCI.HCl (6.3 g, 33.0 mmol) and isoleucine methyl ester (3.0 g, 16.5 mmol). The mixture was allowed to stir at room temperature (25° C.) over 2.5 h under nitrogen atmosphere. The resulting mixture was diluted with DCM (200 mL), washed with water (3×100 mL) and dried over sodium sulphate. The crude product obtained upon evaporation of the solvent was further purified by silica gel column chromatography to obtain product as yellow solid (2.9 g, 72%).

Step 2: Preparation of 3-methyl-2-[pyridine-3-carbonyl-amino]-pentanoic acid

To a solution of 3-methyl-2-[pyridine-3-carbonyl-amino]-pentanoic acid methyl ester (1.5 g, 5.9 mmol), in methanol (10 mL), THF (9 mL), was added LiOH (1.25 g, 29.9 mmol) dissolved in water (3 mL). The mixture was allowed to stir at room temperature (25° C.) over 3 h. Methanol and THF was stripped off from the reaction mass, acidified the reaction mass using 1.5N HCl (pH=2-3). Extracted the reaction mass with ethyl acetate (100 mL) thrice and dried over sodium sulphate and concentrated to obtain product as pale yellow solid (0.7 g, 50%).

Step 3: Preparation of 3-methyl-2-[pyridine-3-carbonyl]amino-pentanoic acid-4-allyl-2-methoxy phenyl ester

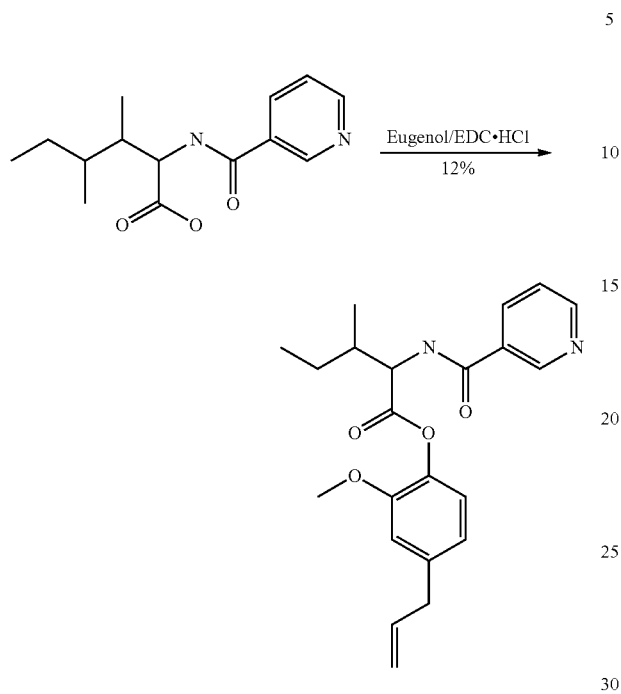

To a solution of 3-methyl-2-[pyridine-3-carbonyl-amino]-pentanoic acid (0.47 g, 1.59 mmol) in DCM (4 mL) were added N-methyl morpholine (9.49 g, 4.9 mmol), EDCI.HCl (0.62 g, 3.28 mmol) and eugenol (0.26 g, 1.59 mmol). The mixture was allowed to stir at room temperature (25° C.) over 4 h under nitrogen atmosphere. The resulting mixture was diluted with DCM (100 mL), washed with water (3×50 mL) and dried over sodium sulphate. The crude product obtained upon evaporation of the solvent was further purified by silica gel column chromatography to obtain required product as white solid (0.12 g, 19.3%).

$^1$H NMR (300 MHz, DMSO-$d_6$) δ (ppm): 0.91-0.98 (m, 3H), 1.06-1.14 (m, 3H), 1.20-1.41 (m, 1H), 1.50-1.70 (m, 1H), 2.09-2.30 (m, 1H), 3.36 (d, J=6.9 Hz, 3H), 3.72 (s, 3H), 4.63-4.87 (m, 1H), 5.04-5.13 (m, 2H), 5.96-5.98 (m, 1H), 6.76-6.79 (m, 1H), 6.95-7.00 (m, 2H), 7.50-7.55 (m, 1H), 8.21-8.25 (m, 1H), 8.72-8.74 (m, 1H), 8.89-9.04 (m, 3H).

LCMS (ESI) m/z: 382.9 ([M+H]$^+$).

Nature of the compound: white solid

Example 7

Preparation of 2-[pyridine-3-carbonyl-amino]-pentane dioic acid-1-(4-allyl-2-methoxy phenyl)ester

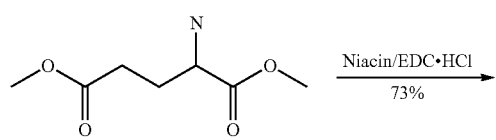

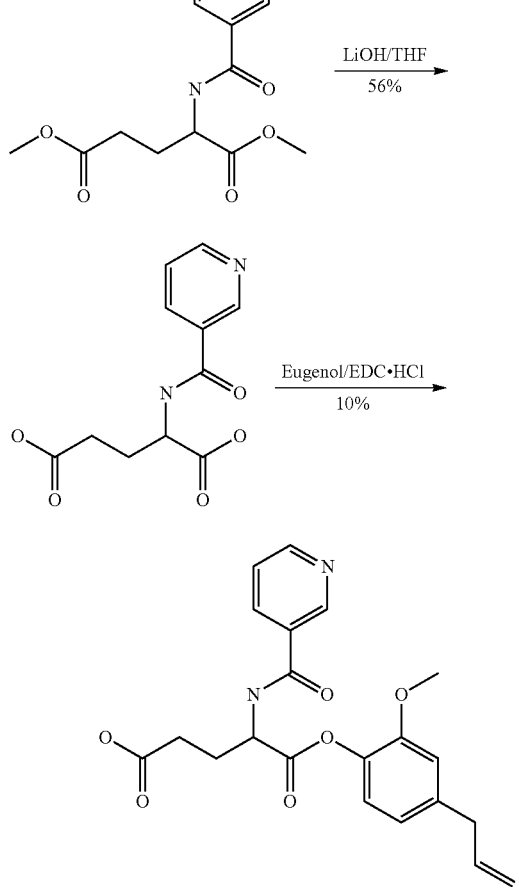

Step 1: Preparation of 2-benzoyl amino-pentane dioic acid dimethyl ester

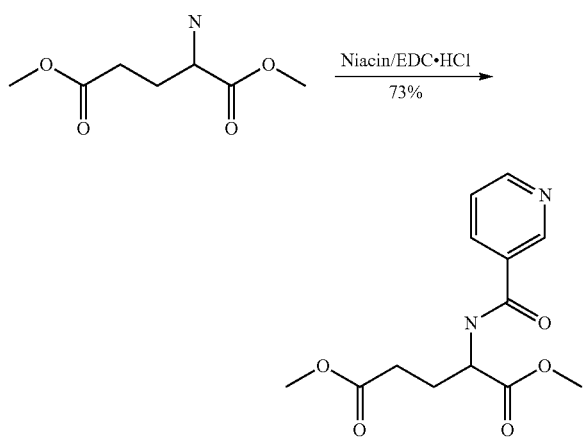

To a solution of niacin (1.4 g, 11.42 mmol) in DCM (20 mL) were added N-methyl morpholine (3.76 mL, 34.2 mmol), EDCI.HCl (4.36 g, 34.2 mmol) and L-glutamic acid dimethyl ester (2.0 g, 11.42 mmol). The mixture was allowed to stir at room temperature (25° C.) over 3 h under nitrogen atmosphere. The resulting mixture was diluted with DCM (100 mL), washed with water (3×50 mL) and dried over sodium sulphate. The crude product obtained upon evaporation of the solvent was further purified by silica gel column chromatography to obtain required product as pale yellow oil (3.1 g, 73%).

Step 2: Preparation of
2-[pyridine-3-carbonyl-amino]-pentanedioic acid

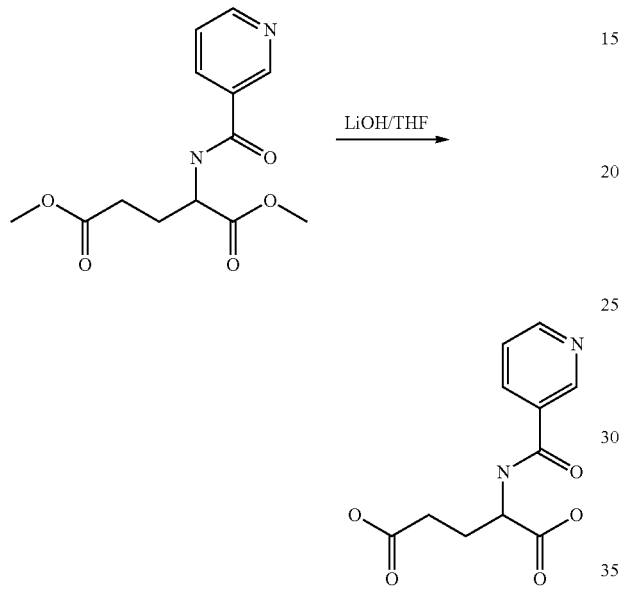

To a solution of 2-benzoyl amino-pentane dioic acid dimethyl ester (0.25 g, 0.89 mmol) in methanol (2 mL), THF (9 mL) was added LiOH (0.037 g, 8.9 mmol) dissolved in water (3 mL). The mixture was allowed to stir at room temperature (25° C.) over 2 h. Stripped off THF, methanol. pH was brought to 1 using 1.5NHCl, reaction mass was extracted with ethyl acetate (100 mL) thrice. Dried over sodium sulphate and concentrated. From the analysis found that mono and di acid formed which was taken as such for next step (1.6 g).

Step 3: Preparation of 2-[pyridine-3-carbonyl-amino]-pentane dioic acid-1-(4-allyl-2-methoxy phenyl)ester

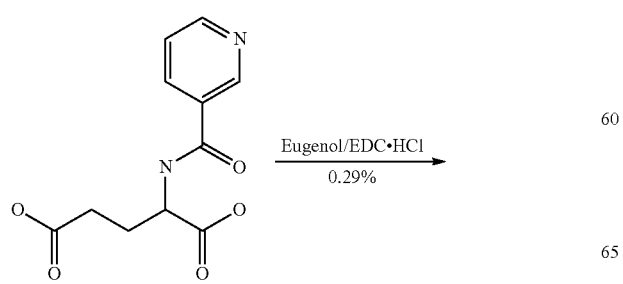

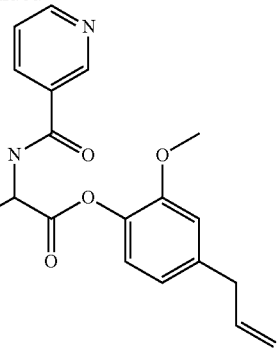

To a solution of di acid (100 mg, 0.42 mmol), in DCM (10 mL) were added N-methyl morpholine (0.085 g, 0.84 mmol), EDCI.HCl (0.097 g, 0.50 mmol) and Eugenol (0.055 g, 0.33 mmol). The mixture was allowed to stir at room temperature (25° C.) over 2 h. The reaction mixture was quenched with water (5 mL) diluted with DCM (100 mL), water washes were given (3×50 mL), dried over sodium sulphate and concentrated. The crude reaction mass was purified by preparative HPLC to obtain pale yellow color solid (0.16 g, 0.29%).

Example 8

Preparation of nicotinic acid 4-allyl-2-methoxy-phenoxycarbonylmethyl ester (Hydrochloride salt)

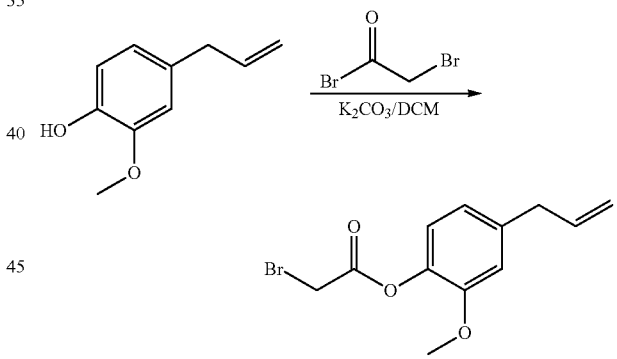

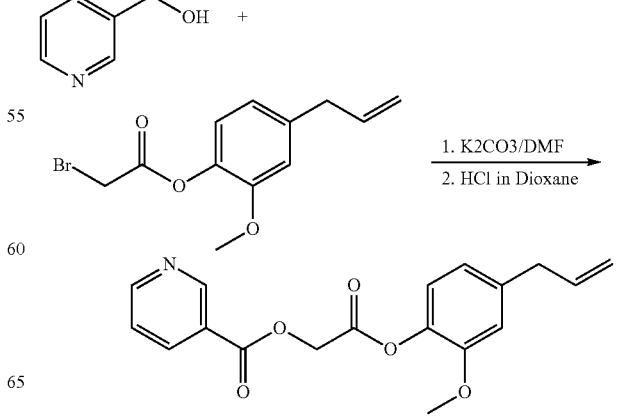

Step 1: Preparation of bromo-acetic acid 4-allyl-2-methoxy-phenyl ester

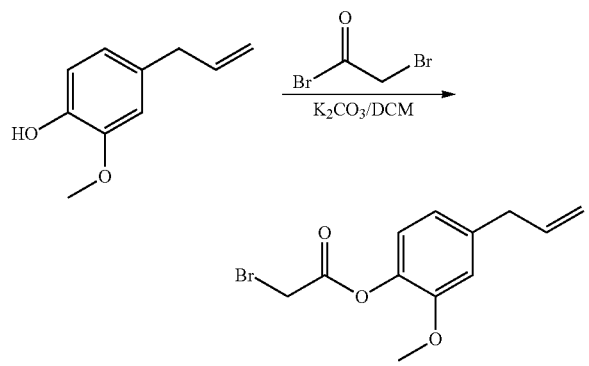

To a solution of eugenol (500 mg, 3.03 mmol) in dichloromethane (5 mL) were added K₂CO₃ (1.0 g, 7.57 mmol) followed by bromo acetyl bromide (931 mg, 4.54 mmol) at 0° C.

The mixture was allowed to stir at room temperature (25° C.) over a period of 1 hr. The resulting mixture was diluted with ethyl acetate (200 mL), washed with water (2×200 mL) and dried over sodium sulphate. The crude product obtained up on evaporation of the solvent was further purified by silica gel column chromatography to obtain bromo-acetic acid 4-allyl-2-methoxy-phenylester as viscous oil (550 mg, 63%).

Step 2: Preparation of Nicotinic acid 4-allyl-2-methoxy-phenoxycarbonylmethyl ester

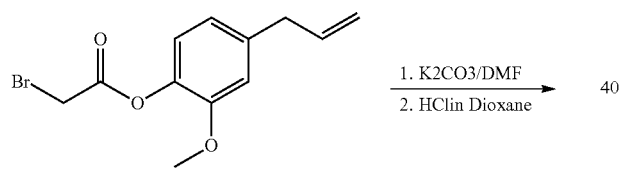

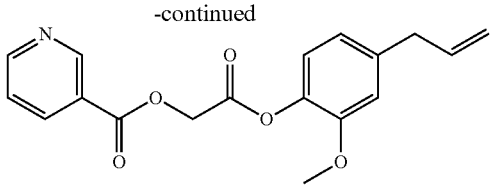

To a solution of nicotinic acid (172 mg, 1.40 mmol) in DMF (4.0 mL) was K₂CO3 (605 mg, 4.38 mmol) at 0° C. To this mixture a solution of compound 1-a (500 mg, 1.75 mmol) in DMF (1.0 mL) was added at same temperature. The reaction mixture was stirred at 25° C. over a period of 60 min. The resulting mixture was diluted with ethyl acetate (400 mL), washed with water (3×200 mL) and dried over sodium sulphate. The crude product obtained up on evaporation of the solvent was further purified by silica gel column chromatography to obtain product as viscous oil (500 mg)

To a solution of above product (500 mg, 1.52 mmol) in diethyl ether (5.0 mL) was added a solution of 4 M HCl in dioxane (0.36 mL, 0.95 mmol) at 0° C. The reaction mixture was allowed stir at room temperature (25° C.) over a period of 90 min to obtain colourless precipitate. The solvent was decanted and dried under reduced pressure to obtain product as colourless solid (450 mg, 85%).

¹H NMR (300 MHz, DMSO-d₆) δ (ppm): 3.37 (d, J=6.9 Hz, 1H), 3.77 (s, 3H), 5.04-5.14 (m, 2H), 5.28 (s, 1H), 5.90-6.02 (m, 1H), 6.77-6.81 (m, 1H), 6.98 (d, J=1.5 Hz, 1H), 7.05-7.07 (m, 1H), 7.71-7.75 (m, 1H), 8.47-8.51 (m, 1H), 8.92-8.94 (m, 1H), 9.21 (d, J=1.2 Hz, 1H).

LCMS (ESI) m/z: 328.2 ([M+H]⁺).

HPLC purity: 99.41%

Nature of the compound: Pale yellow solid

Melting range: 109.3-111.2° C.

Example 9

Preparation of 2-(Pyridine-3-carbonyloxy)-succinic acid 4-(4-allyl-2-methoxy-phenyl) ester 1-methyl ester

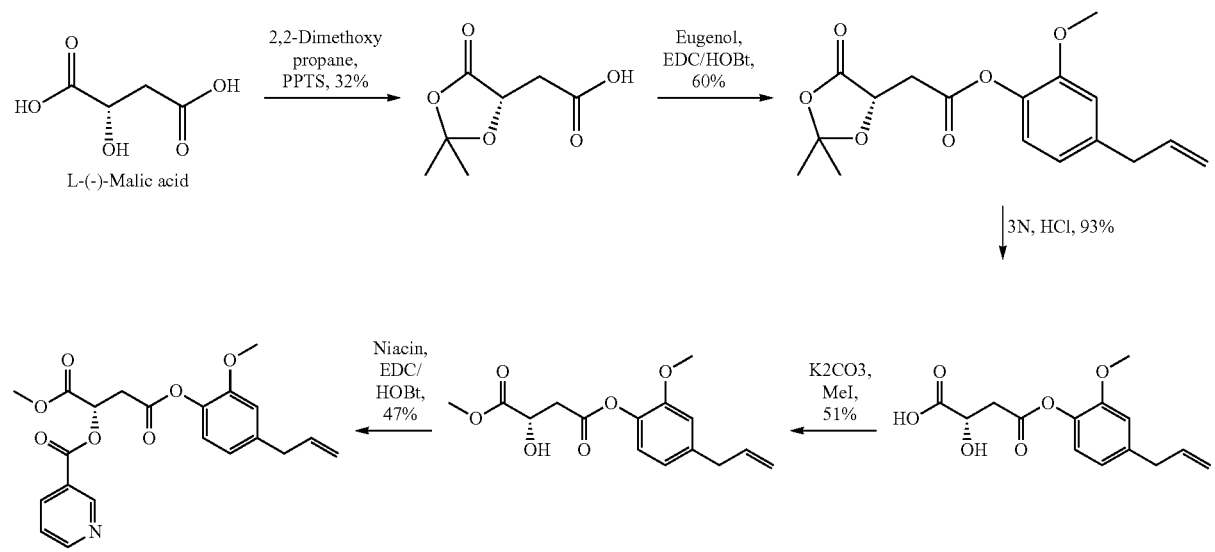

Step 1. Preparation of ((S)-2,2-Dimethyl-5-oxo-[1,3]dioxolan-4-yl)-acetic acid

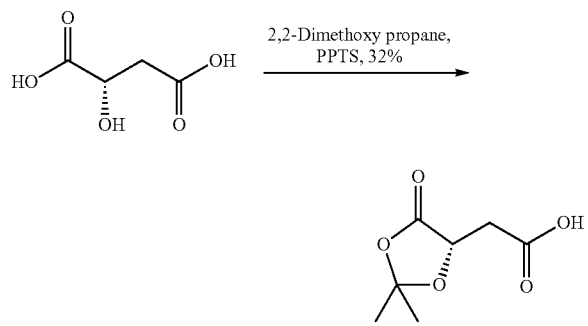

To a suspension of L-(−)-Malic acid (5.0 g, 37.3 mmol) in 2,2-dimethoxy propane (5.0 mL) was added PPTS (0.13 g, 0.5 mmol) at room temperature (25° C.). The reaction mixture stirred at same temperature over a period of 48 h. The resulting mixture was partitioned between water (100 mL) and dichloromethane (250 mL), the aqueous layer was extracted twice with dichloromethane (2×100 mL). The combined organic layers dried ($Na_2SO_4$) and concentrated under reduced pressure to obtain colourless solid (2.1 g, 32%).

Step 2: Preparation of (2,2-Dimethyl-5-oxo-[1,3]dioxolan-4-yl)-acetic acid 4-allyl-2-methoxy-phenyl ester

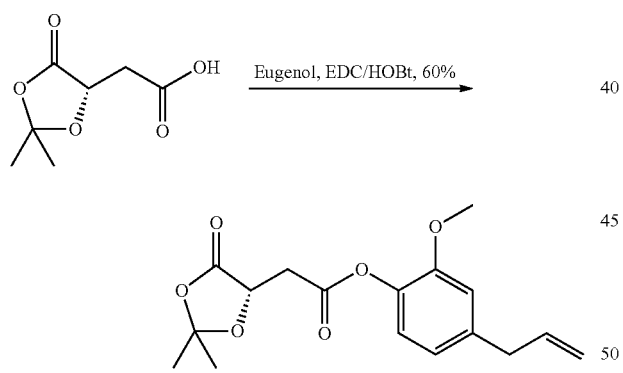

To a solution of ((S)-2,2-Dimethyl-5-oxo-[1,3]dioxolan-4-yl)-acetic acid (2.1 g, 12.0 mmol) in dichloromethane were added N-ethyldiisopropyl amine (10.3 mL), EDCI. HCl (6.9 g, 36.0 mmol), HOBt (1.8 g, 12.0 mmol), DMAP (0.14 g, 1.2 mmol) at ice temperature (0° C.) and the reaction mixture was stirred at same temperature over a period of 15 min. Then eugenol (2.18 g, 13.2 mmol) was added to the reaction mixture at same temperature and the mixture was stirred at room temperature (25° C.) over a period of 12 h. The resulting mixture was diluted with dichloromethane (200 mL), washed with water (4×100 mL), dried ($Na_2SO_4$) and concentrated. The crude product obtained was further purified by column chromatography to obtain colourless solid (2.3 g, 60%).

Step 3: Preparation of 2-Hydroxy-succinic acid 4-(4-allyl-2-methoxy-phenyl) ester

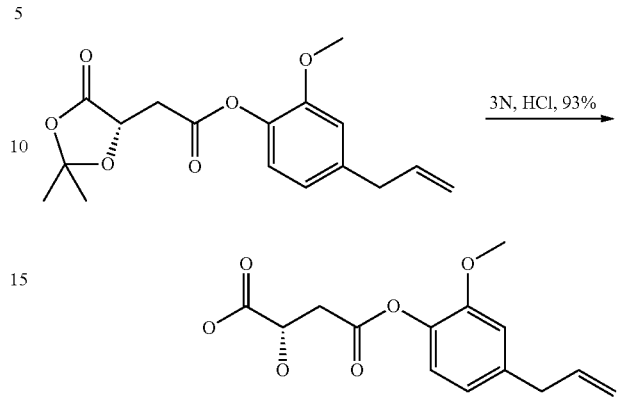

To a solution of (2,2-Dimethyl-5-oxo-[1,3]dioxolan-4-yl)-acetic acid 4-allyl-2-methoxy-phenyl ester (1.0 g, 3.12 mmol) in THF (10.0 mL) was added 1N hydrochloric acid (10 mL) at room temperature (25° C.) and the mixture was stirred at same temperature over a period of 6 h. The solvent was evaporated to half volume, saturated with sodium chloride and the product was extracted with ethyl acetate (2×100 mL). The organic layer was dried over sodium sulphate and concentrated to obtain off-white solid (0.81 g, 93%).

Step 4: Preparation of 2-Hydroxy-succinic acid 4-(4-allyl-2-methoxy-phenyl) ester 1-methyl ester

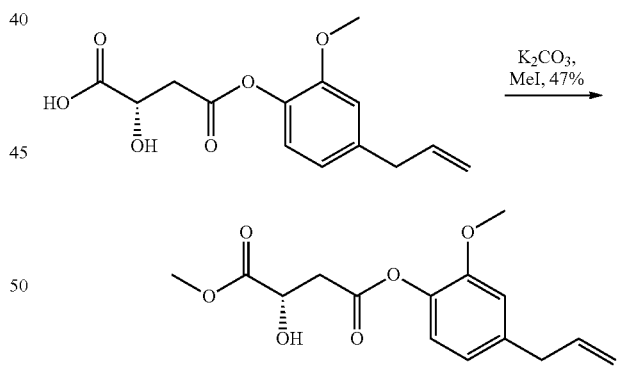

To a solution of 2-Hydroxy-succinic acid 4-(4-allyl-2-methoxy-phenyl) ester (0.1 g, 0.35 mmol) in dry DMF (2.0 mL) was added dry $K_2CO_3$ followed by methyl iodide (0.024 mL) at 0° C. and the reaction mixture was stirred at room temperature (25° C.) over a period of 60 min. The resulting mixture was diluted with ethyl acetate (50.0 mL) and filtered. The filtrate was washed with water (4×200 mL) and dried over sodium sulphate. The crude product obtained upon evaporation of volatiles was purified by column chromatography to obtain orange colour viscous liquid (0.05 g, 47%).

Step 5: Preparation of 2-(Pyridine-3-carbonyloxy)-succinic acid 4-(4-allyl-2-methoxy-phenyl) ester 1-methyl ester

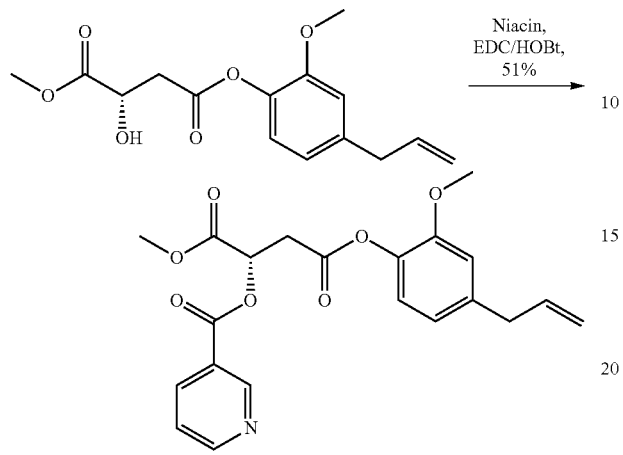

To a suspension of niacin (90 mg, 0.7 mmol) in dichloromethane (10.0 mL) were added N-ethyldiisopropyl amine (0.58 mL, 3.0 mmol), EDCI.HCl (380 mg, 2.0 mmol), HOBt (50 mg, 0.3 mmol) at 0° C. and stirred for 15 min. Then 2-Hydroxy-succinic acid 4-(4-allyl-2-methoxy-phenyl) ester (200 mg, 0.6 mmol) was added at the same temperature and the reaction mixture was stirred at room temperature (25° C.) over a period of 5 h. The reaction mixture was diluted with DCM (150 mL), washed with water (4×50 mL) and dried over sodium sulphate. The crude product obtained upon evaporation of volatiles was purified by column chromatography to obtain pale yellow viscous oil (140 mg, 51%).

$^1$H NMR (300 MHz, CDCl$_3$) δ (ppm): 3.32 (d, J=6.3 Hz, 2H), 3.37 (d, J=6.6 Hz, 2H), 3.73 (s, 3H), 3.84 (s, 3H), 5.07 (s, 1H), 5.10-5.13 (m, 1H), 5.85-5.98 (m, 2H), 6.74-6.76 (m, 2H), 6.92-6.95 (m, 1H), 7.40-7.45 (m, 1H), 8.35-8.39 (m, 1H), 8.82 (d, J=3.6 Hz, 1H), 9.31 (s, 1H).

LCMS (ESI) m/z: 400.0 ([M+H]$^+$).

HPLC purity: 99.23%

Nature of the compound: pale yellow viscous oil, becomes a low melting solid (48° C.) on storage in refrigerator.

Compound 16, the ethyl ester analog of compound 9, having the structure shown below:

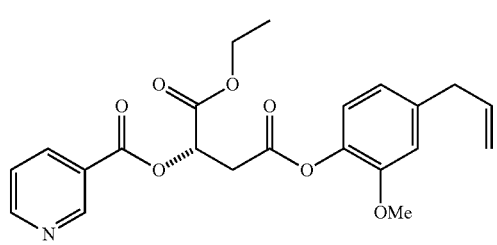

is synthesized using the same synthesis scheme as in compound 9 above, except that in Step 4, ethyl iodide is used in place of methyl iodide.

Nature of Compound 16:
Appearance: Off-white solid;
Melting point: 52.0-55.4° C.;

$^1$H NMR (300 MHz, DMSO-d6) δ (ppm): 1.19 (t, J=6.9 Hz, 3H), 3.31-3.36 (m, 4H), 3.64 (s, 3H), 4.19 (q, J=7.2 Hz, 2H), 5.02-5.12 (m, 2H), 5.70 (t, J=6.0 Hz, 1H), 5.90-5.99 (m, 1H), 6.74-6.77 (m, 1H), 6.70-6.93 (m, 2H), 7.61-7.65 (m, 1H), 8.33 (d, J=7.8 Hz, 1H), 8.86-8.88 (m, 1H), 9.14 (d, J=1.2 Hz, 1H);

LCMS (ESI) m/z: 414.3 ([M+H]+); and

HPLC purity: 97.9%.

Example 10

Preparation of 1-(pyridine-3-carbonyl)-pyrrolidine-2-carboxylic acid 4-allyl-2-methoxy-phenyl ester

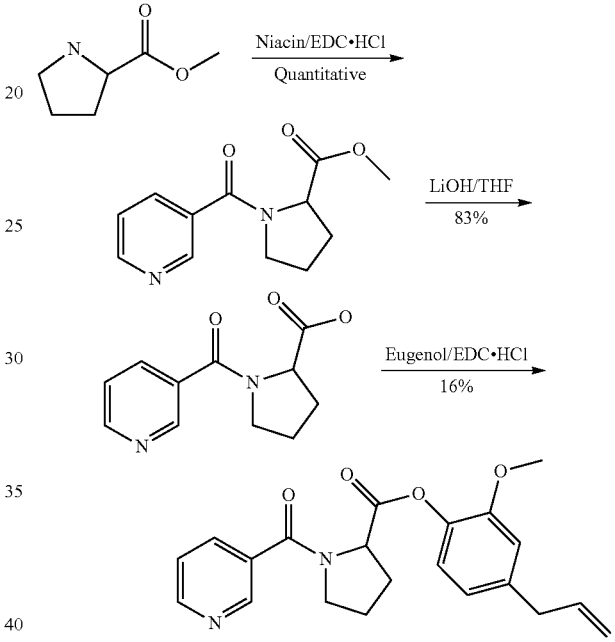

Step 1: Preparation of 1-(pyridine-3-carbonyl)-pyrrolidine-2-carboxylic acid methyl ester

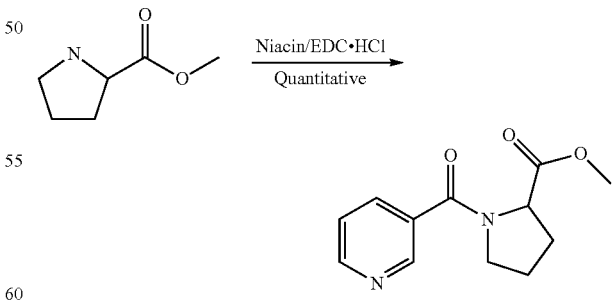

To a solution of niacin (0.4 g 3.50 mmol) in DCM (10 mL) were added L-proline methyl ester (0.5 g, 3.21 mmol), N-methyl morpholine (1.1 mL, 0.10.5 mmol), EDC.HCl (1.2 g, 6.4 mmol) and catalytic amount of DMAP at ice temperature (0° C.). The mixture was allowed to stir at room temperature (25° C.) over a period of 2 h. The resulting mixture diluted with DCM (100 mL) washed with water (2×100 mL) and dried over sodium sulphate. Solvent was evaporated under reduced pressure to obtain product as yellow gummy oil (1.3 g).

Step 2: Preparation of 1-(pyridine-3-carbonyl)-pyrrolidine-2-carboxylic acid

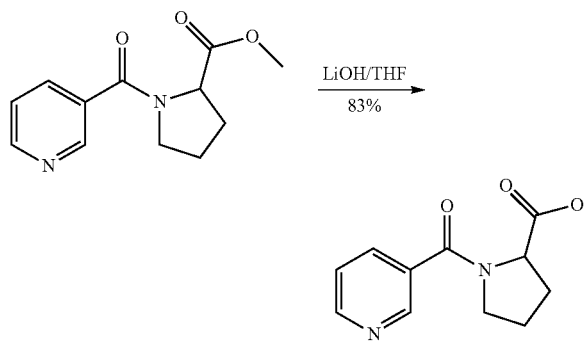

To a solution of 1-(pyridine-3-carbonyl)-pyrrolidine-2-carboxylic acid methyl ester (1.3 g, 5.4 mmol), in THF (13 mL) was added lithium hydroxide (0.34 g, 8.1 mmol) in water (1.3 mL) at room temperature (25° C.). The mixture was allowed to stir at room temperature (25° C.) over a period of 2 h. THF was evaporated from the reaction mixture, dissolve the residue in methanol acidified to pH=4, filtered and evaporated the sticky liquid on evaporation was triturated with diethyl ether, to obtain required compound as off-white solid (1.0 g, 83%).

Step 3: Preparation of 1-(pyridine-3-carbonyl)-pyrrolidine-2-carboxylic acid 4-allyl-2-methoxy-phenyl ester

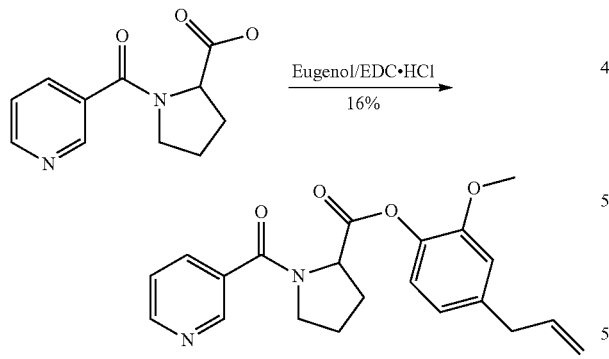

To a solution of Euginol (0.7 g, 4.2 mmol) in DCM (20 mL) was added 1-(pyridine-3-carbonyl)-pyrrolidine-2-carboxylic acid (1 g, 4.6 mmol) followed by N-methyl morpholine (2.7 mL, 25.2 mmol), EDCI.HCl (1.6 g, 8.4 mmol) and catalytic amount of DMAP at room temperature (0° C.). The mixture was allowed to stir at room temperature (25° C.) for over a period of 12 h. The resulting mixture was diluted with DCM (200 mL) washed with water (2×100 mL) and dried over sodium sulphate. The crude product obtained upon evaporation of the solvent was further purified by silica gel column chromatography to obtain resulting product as pale yellow gummy compound (260 mg, 16%).

LCMS (ESI) m/z: 367.0 ([M+H]$^+$).
HPLC purity: 99.26%
Nature of the compound: pale yellow gummy solid Example 11

Preparation of [(pyridine-3-carbonyl)-amino]-acetic acid 4-allyl-2-methoxy-phenyl ester

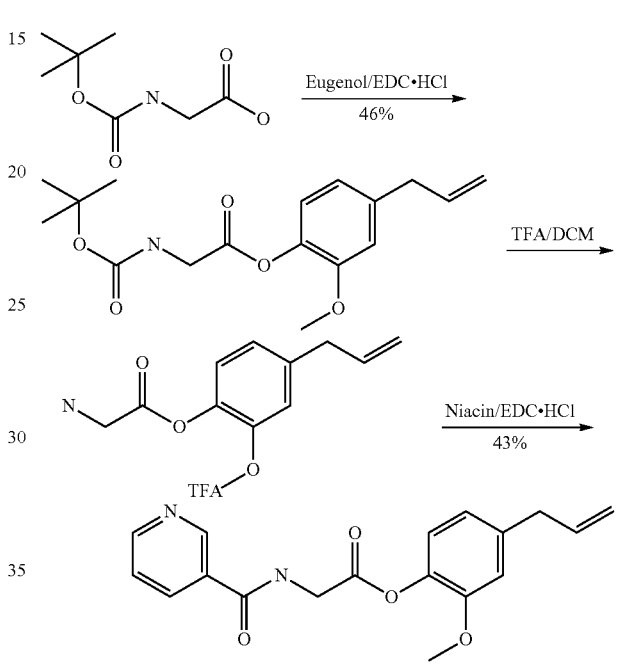

Step 1: Preparation of Amino-acetic acid 4-allyl-2-methoxy-phenyl ester

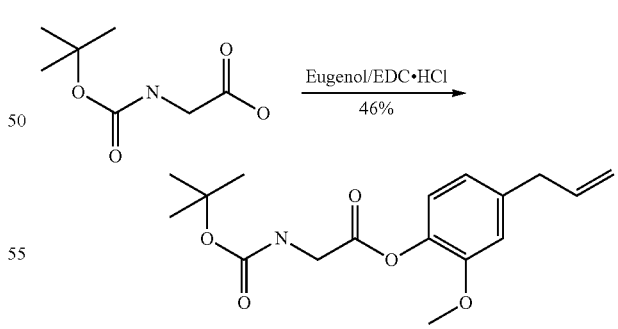

To a solution of Eugenol (0.3 g, 1.82 mmol) in DCM (20 mL), was added Boc-glycine (0.35 g, 2.01 mmol), N-methyl morpholine (0.65 mL, 6.00 mmol), EDC.HCl (0.76 g, 4.0 mmol) and DMAP at ice temperature. The mixture was allowed to stir at room temperature (25° C.) over a period of 12 h. The resulting mixture was diluted with DCM (100 mL), washed with water (2×50 mL) and dried over sodium sulphate. The crude product obtained upon evaporation of the solvent was purified by silica gel column chromatography to obtain resulting product as pale yellow oil (300 mg, 46.9%)

Step 2: Preparation of Amino-acetic acid 4-allyl-2-methoxy-phenyl ester Trifluoroacetate

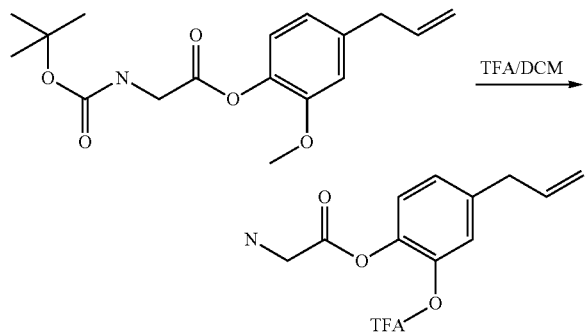

To a solution of compound amino-acetic acid 4-allyl-2-methoxy-phenyl ester (0.3 g) in DCM (10 mL) was added trifluoroacetic acid (0.5 mL) drop wise at (0° C.). The mixture was allowed to stir at room temperature (25° C.) over a period of 2 h. Solvent was stripped off completely and the reaction was carried for the next step (510 mg).

Step 3: Preparation of [(pyridine-3-carbonyl)-amino]-acetic acid 4-allyl-2-methoxy-phenyl ester

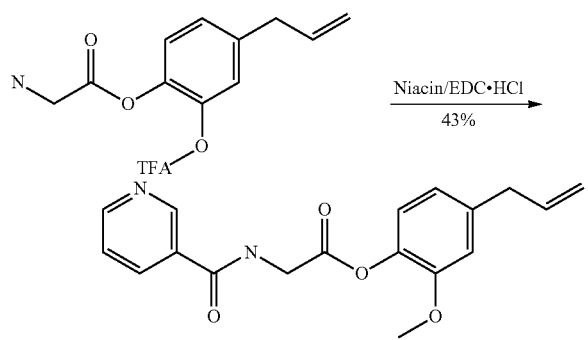

To a solution of Amino-acetic acid 4-allyl-2-methoxy-phenyl ester (510 mg, 1.7 mmol), in DCM (20 mL) were added niacin (0.23 g, 1.9 mmol), N-methyl morpholine (0.96 mL, 8.8 mmol), EDC.HCl (0.67 g, 3.5 mmol) at ice temperature (0° C.). The mixture was allowed to stir at room temperature (25° C.) over a period of 2 hrs. The resulting mixture was diluted with DCM (200 mL) washed with water (2×100 mL) and dried over sodium sulphate. The crude product obtained upon evaporation of the solvent was purified by silica gel column chromatography to obtain product as off-white solid (210 mg, 43%).

$^1$H NMR (300 MHz, CDCl$_3$) δ (ppm): 3.40 (d, J=8.4 Hz, 2H), 3.84 (s, 3H), 4.55 (d, J=5.1 Hz, 2H), 5.09-5.15 (m, 2H), 5.92-6.01 (m, 1H), 6.78-6.83 (m, 2H), 6.96-7.02 (m, 1H), 7.39-7.43 (m, 1H), 8.15-8.19 (m, 1H), 8.74-8.96 (m, 1H), 9.07 (d, J=2.1 Hz, 1H).

LCMS (ESI) m/z: 372.0 ([M+1-1]$^+$).

HPLC purity: 98.25%

Nature of the compound: off-white solid

Example 12

Preparation of (S)-2-hydroxy-succinic acid bis-(4-allyl-2-methoxy-phenyl) ester

Step 1: Preparation of ((S)-2,2-Dimethyl-5-oxo-[1,3]dioxolan-4-yl)-acetic acid

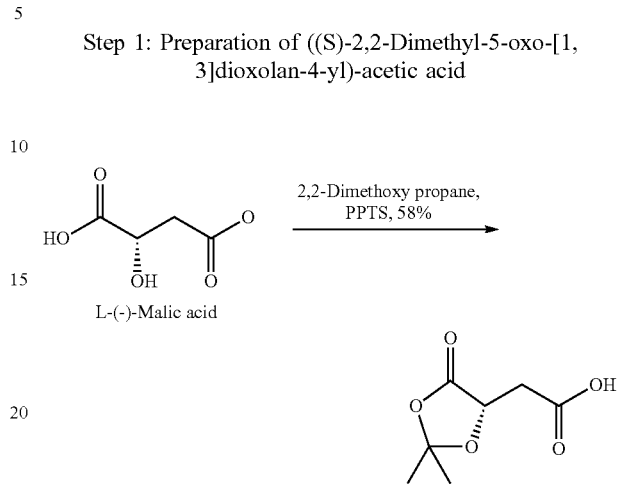

L-(−)-Malic acid

To a suspension of L-(−)-Malic acid (100.0 g, 0.74 mol) in 2,2-dimethoxy propane (200 mL) was added PPTS (2.60 g, 15.11 mmol) at room temperature (25° C.). The reaction mixture stirred at same temperature over a period of 48 h. The resulting mixture was partitioned between water (1.0 L) and dichloromethane (2.5 L), the aqueous layer was extracted twice with dichloromethane (2×500 mL). The combined organic layers dried (Na$_2$SO$_4$) and concentrated under reduced pressure to obtain colourless solid (75.0 g, 58%).

Step 2: Preparation of (2,2-Dimethyl-5-oxo-[1,3] dioxolan-4-yl)-acetic acid 4-allyl-2-methoxy-phenyl ester

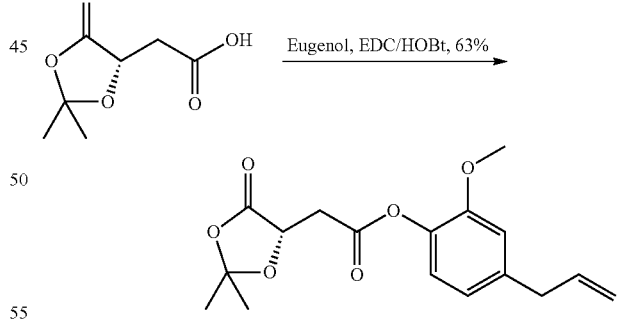

To a solution of ((S)-2,2-Dimethyl-5-oxo-[1,3]dioxolan-4-yl)-acetic acid (30.0 g, 0.17 mol) in dichloromethane (300 mL) were added N-ethyldiisopropyl amine (147 mL, 0.86 mol), EDCI. HCl (98.0 g, 0.51 mol), HOBt (13.1 g, 0.08 mol), DMAP (0.2 g, 0.01 mol) at ice temperature (0° C.) and the reaction mixture was stirred at same temperature over a period of 15 min. Then eugenol (26.1 mL, 0.17 mol) was added to the reaction mixture at same temperature and the mixture was stirred at room temperature (25° C.) over a period of 5 h. The resulting mixture was diluted with dichloromethane (2.0 L), washed with water (4×500 mL), dried (Na₂SO₄) and concentrated. The residue obtained upon evaporation of the solvent was washed with petroleum ether to obtain product as a off-white solid (35.0 g, 63%).

Step 3: Preparation of 2-Hydroxy-succinic acid 4-(4-allyl-2-methoxy-phenyl) ester

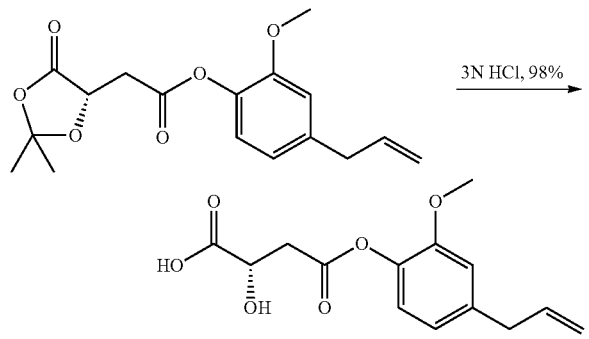

To a solution of (2,2-Dimethyl-5-oxo-[1,3]dioxolan-4-yl)-acetic acid 4-allyl-2-methoxy-phenyl ester (35.0 g, 0.10 mol) in THF (350 mL) was added 1N hydrochloric acid (350 mL) at room temperature (25° C.) and the mixture was stirred at same temperature over a period of 8 h. The solvent was evaporated to half volume, saturated with sodium chloride and the product was extracted with ethyl acetate (2×850 mL). The organic layer was dried over sodium sulphate and concentrated to obtain off-white solid (30.0 g, 98%).

Step 4: Preparation of (S)-2-hydroxy-succinic acid bis-(4-allyl-2-methoxy-phenyl) ester

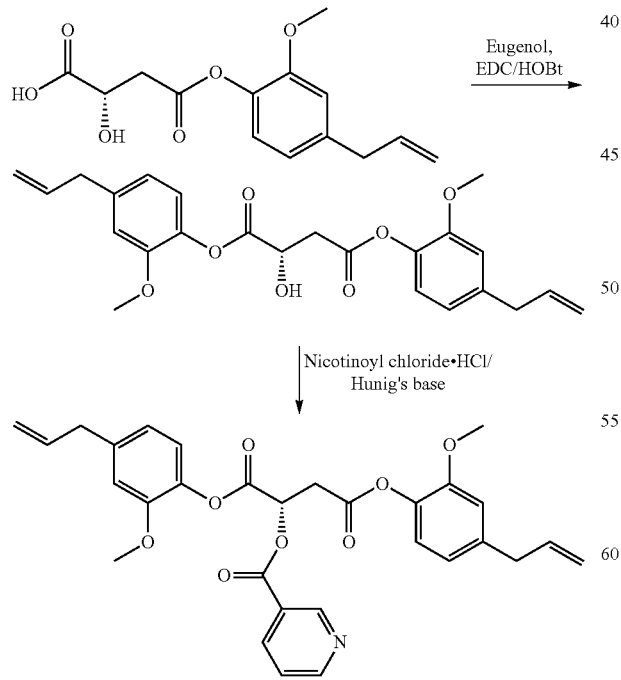

To a solution of 2-Hydroxy-succinic acid 4-(4-allyl-2-methoxy-phenyl) ester (20.0 g, 0.07 mol) in dichloromethane (450 mL) was added N-ethyldiisopropyl amine (61.0 mL, 0.35 mol), EDCI·HCl (40.8 g, 0.21 mol), HOBt (5.4 g, 0.03 mmol), DMAP (87 mg, 0.7 mmol) at ice temperature (0° C.) and the reaction mixture were stirred at same temperature over a period of 15 min. Then eugenol (11.7 g, 0.07 mol) was added to the reaction mixture at same temperature and the mixture was stirred at room temperature (25° C.) over a period of 2 h.

To the above reaction mixture was added N-ethyldiisopropyl amine (24.0 mL, 0.14 mol) followed by nicotinoyl chloride hydrochloride (25.4 g, 0.14 mol) was added at ice temperature (0° C.) and the mixture was stirred at room temperature (25° C.) over a period of 2 h. The resulting mixture was diluted with ethyl acetate (2.0 L), washed with water (4×1.0 L), dried (Na₂SO₄) and concentrated. The crude product obtained was further purified by column chromatography to obtain yellow viscous liquid (10.02 g, 37%).

¹H NMR (300 MHz, DMSO-d₆) δ (ppm): 3.34-3.38 (m, 4H), 3.53-3.55 (m, 2H), 3.65 (s, 3H), 3.75 (s, 3H), 5.04-5.08 (m, 2H), 5.13 (s, 1H), 5.14 (s, 1H), 5.92-6.02 (m, 3H), 6.77-6.80 (m, 2H), 6.95-7.06 (m, 4H), 7.63-7.67 (m, 1H), 8.36-8.40 (m, 1H), 8.88-8.90 (m, 1H), 9.18 (s, 1H).

LCMS (ESI) m/z: 532.1 ([M+H]⁺).

HPLC purity: 98.42%

Nature of the compound: Pale yellow viscous oil

Example 13

Preparation of 4[(pyridine-3-carbonyl)-amino]-butyric acid-4-allyl-2-methoxy phenyl ester

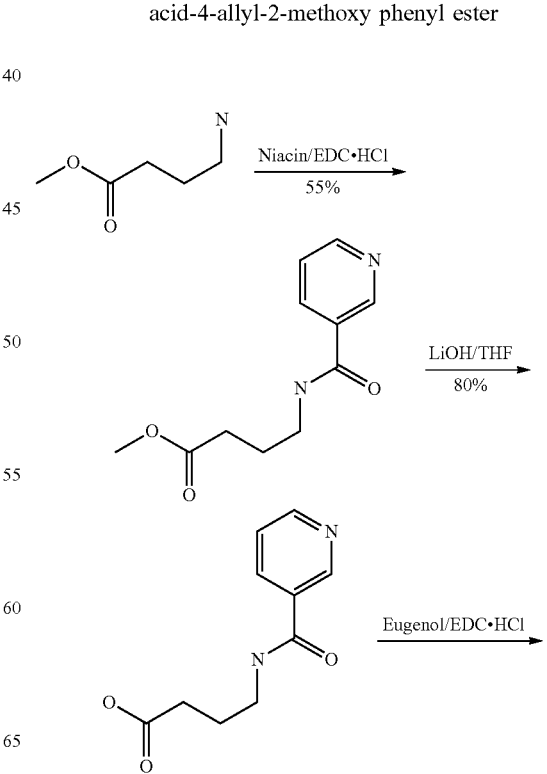

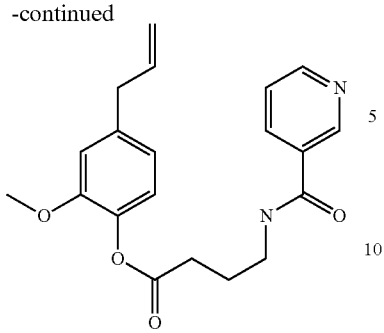

Step 1: Preparation of 4[(pyridine-3-carbonyl)-amino]-butyric acid methyl ester

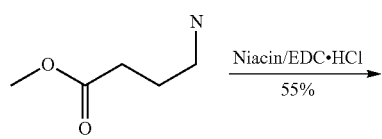

To a solution of nicotinic acid (1.6 g, 13.0 mmol), were added N-methyl morpholine (4.29 mL, 39.04 mmol), EDCI·HCl (4.0 g, 26.0 mmol) and amine (2.0 g, 13.00 mmol). The mixture was allowed to stir at room temperature (25° C.) over 3 h under nitrogen atmosphere. The resulting mixture was diluted with DCM (200 mL), washed with water (2×100 mL) and dried over sodium sulphate. The crude product obtained upon evaporation of the solvent was further purified by silica gel column chromatography to obtain required product as white solid (1.59 g, 55%).

Step 2: Preparation of 4[(pyridine-3-carbonyl)-amino]-butyric acid

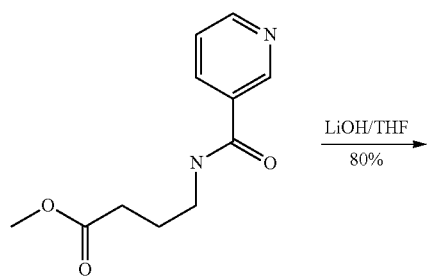

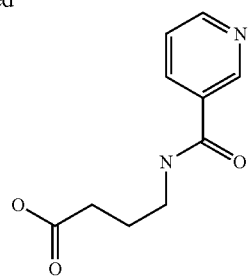

To a solution of 4[(pyridine-3-carbonyl)-amino]-butyric acid methyl ester (0.8 g, 3.5 mmol), in THF (14 mL) was added LiOH (0.75 g, 17.9 mmol), dissolved in water (6 mL). The mixture was allowed to stir at room temperature (25° C.) overnight. 50% starting material remains as such. Then reaction mixture heated at (45° C.). The reaction did not progress. The reaction mixture was worked up with chloroform to recover the starting material. The aqueous layer was diluted with water, acidified with 1.5N HCl till (pH=2-3), extracted with ethyl acetate (150 mL) and dried over sodium sulphate, concentrated to obtain yellow colour solid (0.6 g, 80%).

Step 3: Preparation of 4[(pyridine-3-carbonyl)-amino]-butyric acid-4-allyl-2-methoxy phenyl ester

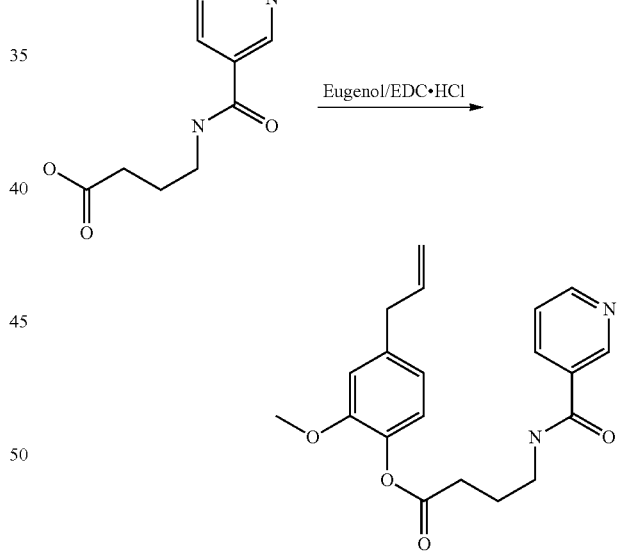

To a solution of 4[(pyridine-3-carbonyl)-amino]-butyric acid (0.6 g, 2.8 mmol) in DMF (10 mL) were added N-methyl morpholine (0.9 mL, 8.6 mmol), EDCI.HCl (1.1 g, 5.7 mmol) and eugenol (0.4 mL, 4.8 mmol). The mixture was allowed to stir at room temperature (25° C.) over night under nitrogen atmosphere. The resulting mixture was diluted with ethylacetate (200 mL), washed with water (4×100 mL) and dried over sodium sulphate. The crude product obtained upon evaporation of the solvent was further purified by preparative HPLC to obtain required product as colorless solid.

LCMS (ESI) flak: 355.1 ([M+H]$^+$).

Nature of the compound: colorless solid

Example 14

Preparation of 4-allyl-2-methoxyphenyl 2-(nicotinamido) propanoate

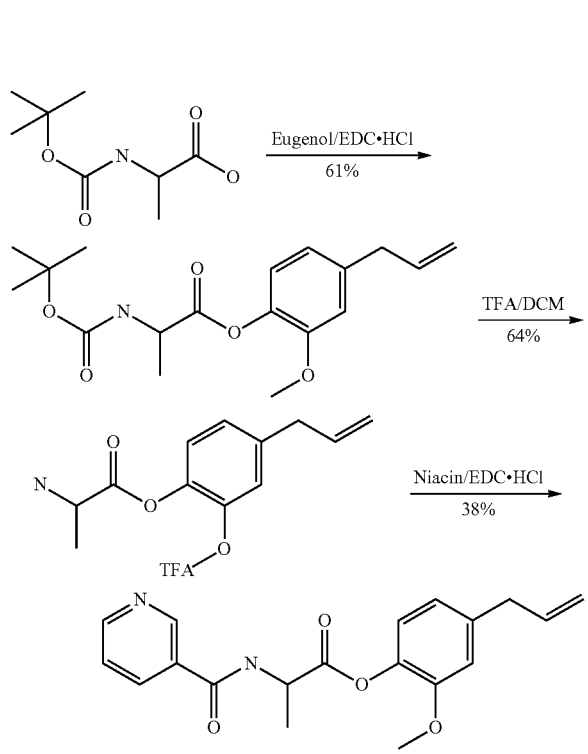

Step 1: Preparation of 2-tert-butoxycorbonylamino-propionic acid-4-allyl-2-methoxy-phenyl ester

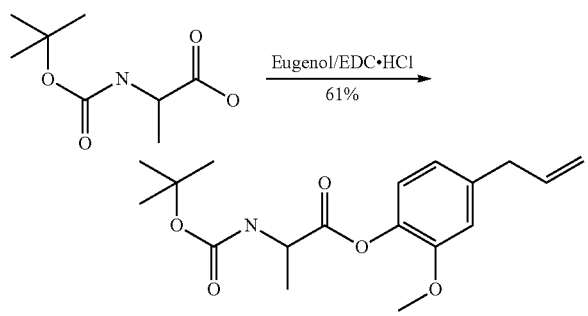

To a solution of N-Boc-alanine (3 g, 14.7 mmol) in DCM (30 mL) were added EDC.HCl (3.73 g, 29.5 mmol), N-methyl morpholine (2.86 mL, 44.2 mmol) and eugenol (1.5 mL, 14.7 mmol) at ice temperature (0° C.). The mixture was allowed to stir at room temperature (25° C.) over a period of 2 h under nitrogen. The resulting mixture was diluted with DCM (300 mL), washed with water (3×100 mL) and dried over sodium sulphate. The crude product obtained upon evaporation of the solvent was further purified by silica gel column chromatography to obtain resulting product as off white solid (3 g, 61%).

Step 2: Preparation of 2[(pyridine-3-carbonyl)-amino]-propionic acid -4-allyl-2-methoxy-phenylester

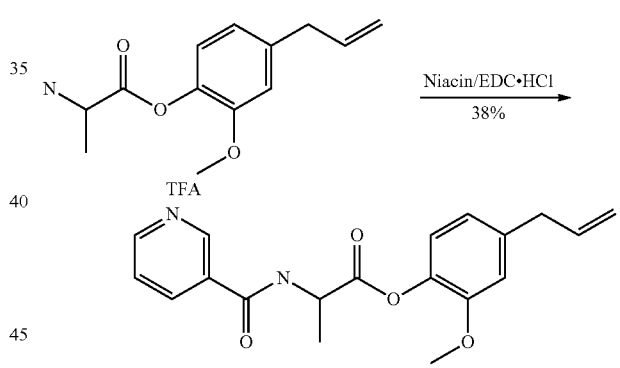

To a solution of 2-tert-butoxycorbonylamino-propionic acid-4-allyl-2-methoxy-phenyl ester (1.0 g, 2.9 mmol) in DCM (10 mL) was added trifluoroacetic acid (1.0 g, 8.9 mmol) drop wise at (0° C.). The mixture was allowed to stir at room temperature (25° C.) over a period of 2 h under nitrogen and stripped off TFA under vacuum, the pH of the crude mass was adjusted to 6-7 by bicarbonate solution. Free amine was extracted with ethyl acetate (100 mL) and dried over sodium sulphate and concentrated to obtain off white solid (0.45 g, 64%).

Step 3

To a solution of nicotinic acid (0.280 g, 0.42 mmol) in DCM (6 mL) were added EDCl.HCl (0.876 g, 0.85 mmol) N-methyl morpholine (0.74 mL, 1.27 mmol) and 2[(pyridine-3-carbonyl)-amino]-propionic acid -4-allyl-2-methoxy-phenylester (0.543 g, 0.42 mmol) under nitrogen. The mixture was allowed to stir at room temperature (25° C.) over a period of 2 hrs under nitrogen. The resulting mixture was diluted with DCM (100 mL), washed with water (3×50 mL) and dried over sodium sulphate. The crude product obtained upon evaporation of the solvent was further purified by silica gel column chromatography to obtain resulting product as white solid (0.30 g, 38.4%).

$^1$H NMR (300 MHz, CDCl$_3$) δ (ppm): 1.79 (d, J=7.2 Hz, 3H), 3.38-3.44 (m, 2H), 3.83 (s, 3H), 4.38 (bs, 1H), 5.02-5.14 (m, 3H), 5.89-6.02 (m, 1H), 6.76-6.78 (m, 2H), 6.85-7.02 (m, 1H), 7.60 (bs, 1H), 8.10 (bs, 1H), 8.57 (bs, 1H), 8.77 (bs, 1H), 9.56 (s, 1H).

LCMS (ESI) m/z: 341.0 ([M+H]$^+$).

HPLC purity: 92.07%

Nature of the compound: white solid

Example 15

Preparation of 4-methyl-2-[pyridine-3-carbonyl]-amino-pentanoic acid-4-allyl-2-methoxy phenyl ester

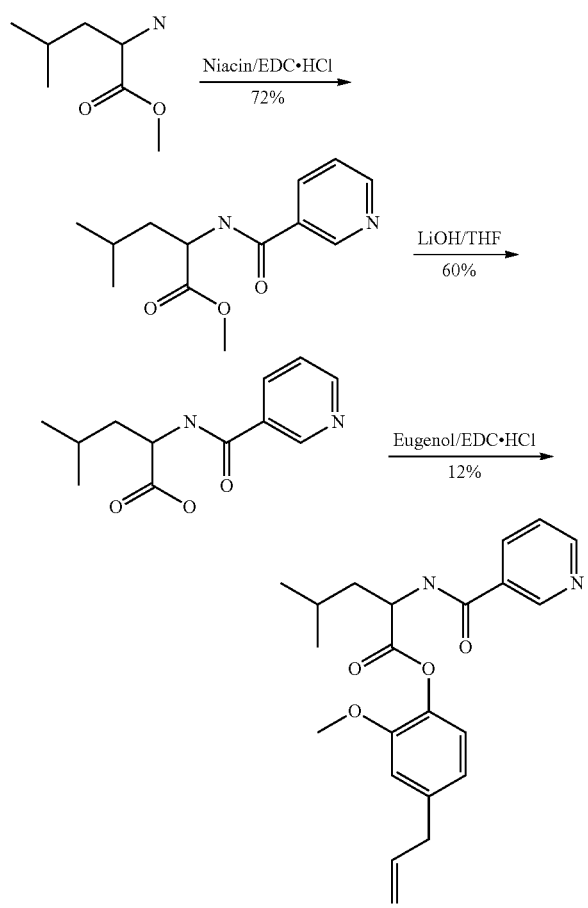

Step 1: Preparation of 4-methyl-2-[pyridine-3-carbonyl]-amino-pentanoic acid methyl ester

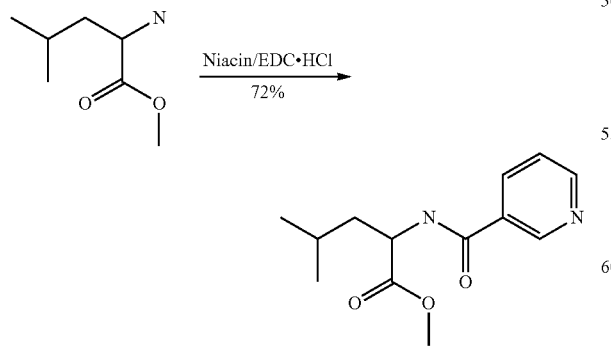

To a solution of niacin (1.35 g, 11.0 mmol) in DCM (20 mL) were added N-methyl morpholine (3.34 g, 33.00 mmol) EDCI.HCl (4.2 g, 22.02 mmol), and L-leucinemethyl ester hydrochloride (2.0 g, 11.0 mmol). The mixture was allowed to stir at room temperature (25° C.) over 2.5 h under nitrogen atmosphere. The resulting mixture was diluted with DCM (200 mL), washed with water (3×100 mL) and dried over sodium sulphate. The crude product obtained upon evaporation of the solvent was further purified by silica gel column chromatography to obtain required product as white solid (2.0 g, 72%).

Step 2: Preparation of 4-methyl-2-[pyridine-3-carbonyl]-amino-pentanoic acid

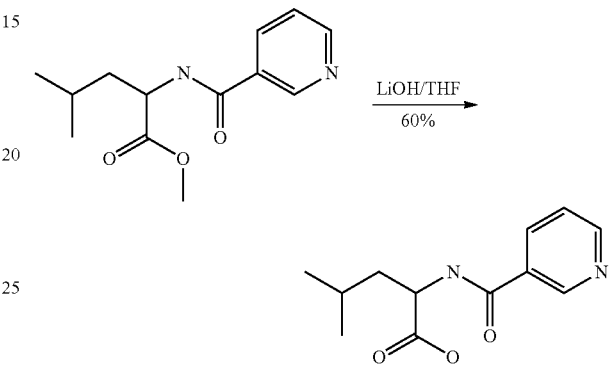

To a solution of 4-methyl-2-[pyridine-3-carbonyl]-amino-pentanoic acid methyl ester (0.80 g, 3.3 mmol), in methanol (8 mL), THF (3 mL) was added LiOH (0.7 g, 16.9 mmol), dissolved in water (9 mL). The mixture was allowed to stir at room temperature (25° C.) over 2.5 h. Methanol and THF was stripped off from the reaction mass, acidified the reaction mass using 1.5NHCl (pH=1). Extracted the reaction mass with ethyl acetate (100 mL) thrice and dried over sodium sulphate and concentrated to obtain product as pale yellow solid (0.45 g, 60%).

Step 3: Preparation of 4-methyl-2-[pyridine-3-carbonyl]-amino-pentanoic acid-4-allyl-2-methoxy phenyl ester

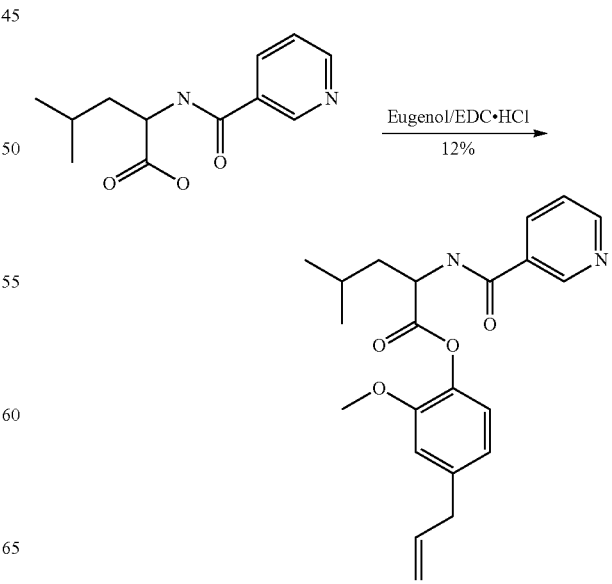

To a solution of 4-methyl-2-[pyridine-3-carbonyl]-aminopentanoic acid (0.47 g, 1.99 mmol) in DCM (5 mL) were added N-methyl morpholine (0.6 mL, 5.99 mmol), EDCI-.HCl (0.76 g, 3.99 mmol) and eugenol (0.32 mL, 1.99 mmol). The mixture was allowed to stir at room temperature (25° C.) over 2.5 h under nitrogen atmosphere. The resulting mixture was diluted with DCM (100 mL), washed with water (3×50 mL) and dried over sodium sulphate. The crude product obtained upon evaporation of the solvent was further purified by silica gel column chromatography to obtain required product as white solid (0.09 g, 12%).

$^1$H NMR (300 MHz, DMSO-$d_6$) δ (ppm): 0.94-0.99 (m, 6H), 1.79-1.93 (m, 3H), 3.36 (d, J=9.3 Hz, 2H), 3.73 (s, 3H), 4.75 (bs, 1H), 5.04-5.14 (m, 2H), 5.92-5.98 (m, 1H), 6.75-6.78 (m, 1H), 6.95-7.00 (m, 2H), 7.51-7.56 (m, 1H), 8.23-8.27 (m, 1H), 8.72-8.74 (m, 1H), 8.05-9.12 (m, 2H).

LCMS (ESI) m/z: 383.0 ([M+H]$^+$).

HPLC purity: 98.59%

Nature of the compound: white solid

Reduction of Aβ42 Production by Compounds in Human Neuronal SH-SY5Y Cells:

Cells were incubated overnight with increasing concentrations the compounds. The cell media was then harvested and Aβ42 in the media was quantitated using sandwich ELISA. The results are shown in Table 1,

TABLE 1

Effect of compounds in blocking Aβ42 secretion

| Compound No. | Structure | Aβ42 IC50 (μM) |
|---|---|---|
| 1 | | >52.25 |
| 2 | | >52.25 |
| 3 | | >52.25 |
| 4 | | >52.25 |
| 5 | 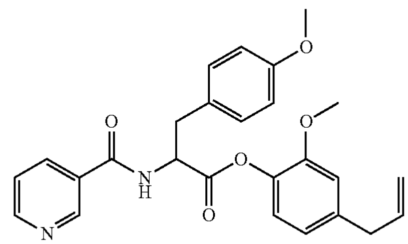 [SMILES: C=CCc1ccc(OC(=O)C(Cc2ccc(OC)cc2)NC(=O)c2cccnc2)c(OC)c1] | >52.25 |
| 6 | 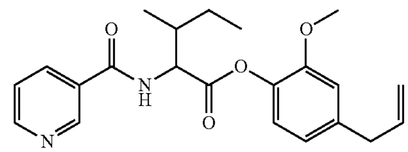 [SMILES: C=CCc1ccc(OC(=O)C(NC(=O)c2cccnc2)C(C)CC)c(OC)c1] | >52.25 |
| 7 | 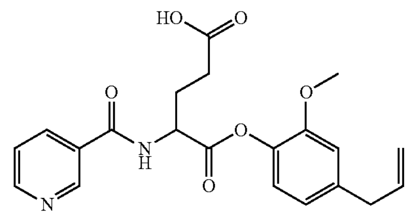 [SMILES: C=CCc1ccc(OC(=O)C(CCC(=O)O)NC(=O)c2cccnc2)c(OC)c1] | >52.25 |
| 8 | 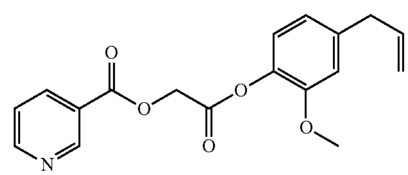 [SMILES: C=CCc1ccc(OC(=O)COC(=O)c2cccnc2)c(OC)c1] | >15.0 |
| 9 | 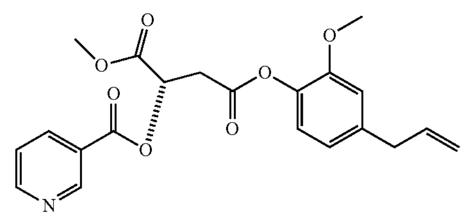 | 18.67 |
| 10 | 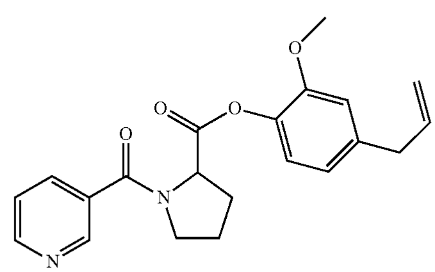 [SMILES: C=CCc1ccc(OC(=O)C2CCCN2C(=O)c2cccnc2)c(OC)c1] | 33.4 |
| 11 | 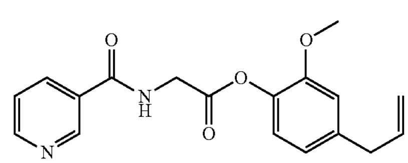 | 15.9 |

TABLE 1-continued

Effect of compounds in blocking Aβ42 secretion

| Compound No. | Structure | Aβ42 IC50 (μM) |
|---|---|---|
| 12 | 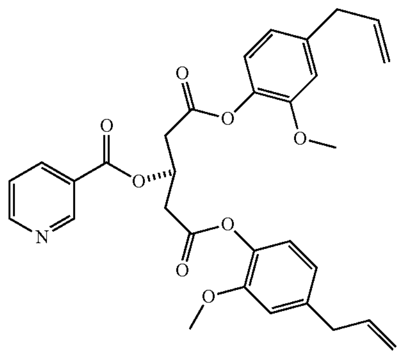 | >52.25 |
| 13 | 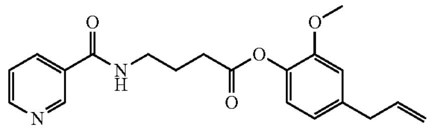 [SMILES: C=CCc1ccc(OC(=O)CCCNC(=O)c2cccnc2)c(OC)c1] | 26.1 |
| 14 | 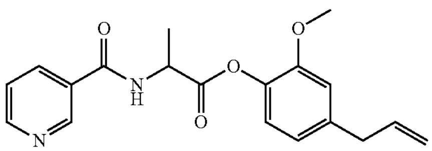 [SMILES: C=CCc1ccc(OC(=O)C(C)NC(=O)c2cccnc2)c(OC)c1] | 15.36 |
| 15 | 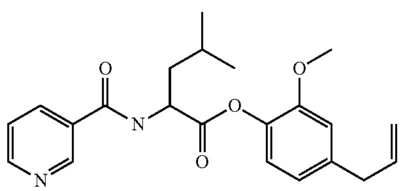 [SMILES: C=CCc1ccc(OC(=O)C(CC(C)C)NC(=O)c2cccnc2)c(OC)c1] | >52.25 |

Figure 2:
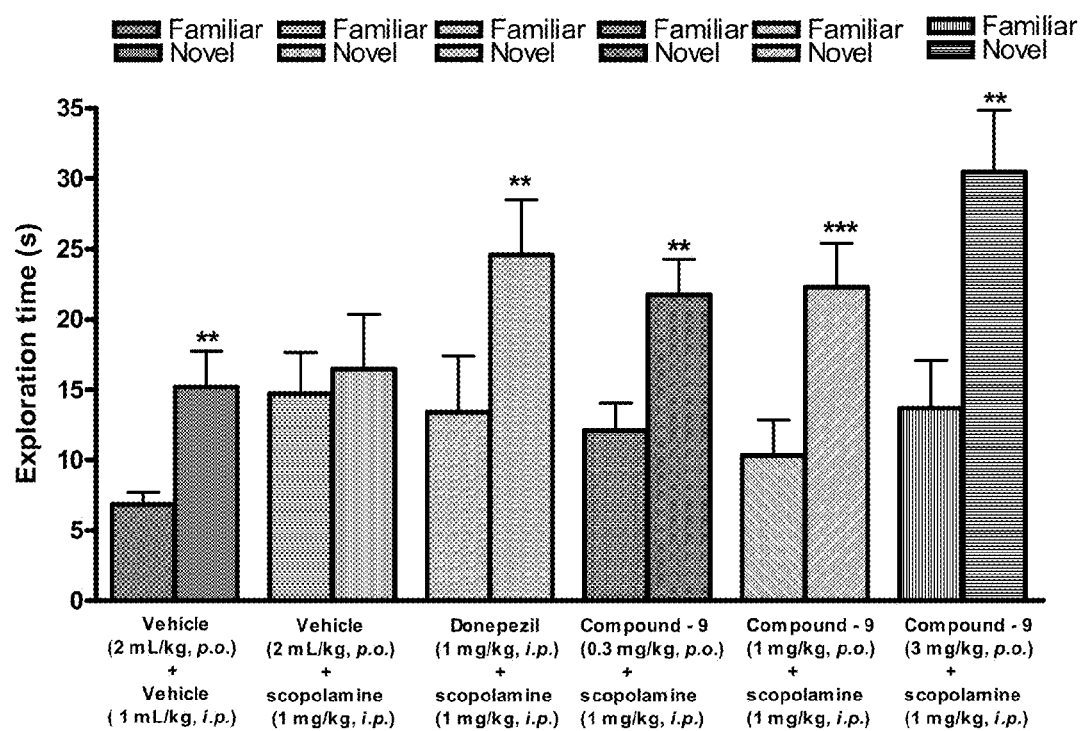
FIG. 2. Effect of compound 9 in improving cognitive function in rat novel object recognition test. Mean (±S.E.M) effect of vehicle (2 mL/kg, p.o.)+vehicle (1 mL/kg, i.p.), vehicle (2 mL/kg, p.o.)+Scopolamine (1 mg/kg, i.p.), Donepezil (1 mg/kg, i.p.)+Scopolamine (1 mg/kg, i.p.), Compound-9 (0.3 mg/kg, p.o.)+Scopolamine (1 mg/kg, i.p.), Compound-9 (1 mg/kg, p.o.)+Scopolamine (1 mg/kg, i.p.) and Compound-9 (3 mg/kg, p.o.)+Scopolamine (1 mg/kg, i.p.) on time spent exploring the novel and familiar object.

Compound 9 Enhances Cognitive Function in Rat Novel Object Recognition Test (NORT):

COMPOUND 9 was tested in NORT test as described in Methods above. Essentially the compound was shown to improve cognitive function as described in their ability to discriminate between a familiar and novel object at all doses tested (0-90 mg/kg/day) and the improvements were similar or greater than a positive control donpezil (FIGS. 1 and 2 shown below)

Effect of Compound 9 on Rat Brain Levels of Aβ-42

After treatment of rats for two weeks, the soluble 4-42 levels in brain (Table 2) were estimated and shown in table below. There was a dose dependent decrease by the compound in levels of this peptide suggesting therapeutic lowering.

TABLE 2

Aβ-42 levels in brain after treatment of rat with Compound 9

| Treatment group | Aβ-42 levels (ng/mg protein) Mean ± SE | Percentage change |
|---|---|---|
| Control | 56.51 ± 7.57 | |
| Simvastatin, 250 mg/kg | 60.83 ± 7.65 | 8 |
| COMPOUND 9, 10 mg/kg | 44.14 ± 7.88 | −22 |
| COMPOUND 9, 25 mg/kg | 31.03 ± 3.98* | −45 |
| COMPOUND 9, 50 mg/kg | 21.85 ± 1.75** | −61 |

$P < 0.05$, **$P < 0.001$, One way ANOVA followed by Dunnett's test compared to Control.
Note:
Simvastatin group was terminated on day 12.

Effect of Compound 9 on Cognition in Morris Water Maze Test:

The results from morris water maze study (as provided in the methods) are shown in Table 3. A measure of improved cognition is the time taken to reach target quadrant by the animals. The latency to target of the vehicle treated group was significantly less compared with scopolamine treated group on $1^{st}$, $2^{nd}$, $3^{rd}$ and $4^{th}$ day. Path length and swim speed of vehicle treated group was significantly less compared with scopolamine treated group on all the 4 days. Similarly a significant decrease in latency and path length to target was observed on $2^{nd}$, $3^{rd}$ and $4^{th}$ day in the group treated with Donepezil compared to scopolamine treated group.

In the COMPOUND 9 (3 mg/kg, p.o.) treated group a significant decrease in latency to target was observed on $1^{st}$, $2^{nd}$, $3^{rd}$ and $4^{th}$ day and a significant decrease in path length to target was observed on $3^{rd}$ and $4^{th}$ day compared to scopolamine treated group. In the COMPOUND 9 (1 mg/kg, p.o.) treated group a significant decrease in path length to target was observed on $3^{rd}$ day compared to scopolamine treated group, the observed effect could be attributed to procognitive property (since no change in swim speed). In the COMPOUND 9 (1 mg/kg, p.o.) treated group a significant decrease in path length to target was observed on $4^{th}$ day compared to scopolamine treated group. The swim speed of the COMPOUND 9 (3 & 10 mg/kg, p.o.) treated group was significantly lesser on $3^{rd}$ day compared to the scopolamine treated group. No significant difference in swim speed was observed between the Donepezil and Scopolamine treated group. In the COMPOUND 9 (10 mg/kg, p.o.) treated group a significant decrease in path length to target was observed on $4^{th}$ day compared to scopolamine treated group.

During the probe trial vehicle treated animals spent significantly more time in the target quadrant compared to the scopolamine treated group. However no significant difference was observed between the compound 9 and Donepezil when compared to Scopolamine treated group. No significant difference in swim speed was observed between the Vehicle, Scopolamine Donepezil and compound 9 treated groups.

In conclusion given the improvements especially in latency to target, compound 9 shows procognitive property and could be a potential to treat cognitive disorders.

TABLE 3

Mean (±S.E.M) effect of COMPOUND 9 on the target latency, swim speed and path length in the water maze in acquisition trials and percent time spent in target quadrant and swim speed in probe trial.

| Day | Group | Values | Target latency (ms) | Swim speed (cm/s) | Path length (cm) |
|---|---|---|---|---|---|
| Day-1 | Vehicle (2 mL/kg, p.o) | Mean<br>SEM | 49303.75^<br>2514.12 | 22.27*<br>0.67 | 1078.92<br>60.55 |
| | Scopolamine (0.5 mg/kg, s.c.) | Mean<br>SEM | 56949.50<br>1593.09 | 26.04<br>0.77 | 1508.81<br>62.20 |
| | Donepezil (3 mg/kg, s.c.) | Mean<br>SEM | 53015.29<br>2170.12 | 24.60<br>0.84 | 1321.73<br>71.87 |
| | Compound 9 (1 mg/kg, p.o.) | Mean<br>SEM | 53859.40<br>2287.66 | 26.53<br>0.75 | 1423.43<br>74.17 |
| | Compound 9 (3 mg/kg, p.o.) | Mean<br>SEM | 50283.22^<br>2821.08 | 25.77<br>0.86 | 1329.08<br>87.59 |
| | Compound 9 (10 mg/kg, p.o.) | Mean<br>SEM | 54445.94<br>2383.13 | 26.93<br>0.72 | 1480.57<br>77.90 |
| Day-2 | Vehicle (2 mL/kg, p.o) | Mean<br>SEM | 31236.14*<br>3273.45 | 22.93*<br>0.81 | 709.49***<br>76.79 |
| | Scopolamine (0.5 mg/kg, s.c.) | Mean<br>SEM | 57037.77<br>1710.81 | 30.12<br>0.85 | 1745.79<br>70.90 |
| | Donepezil (3 mg/kg, s.c.) | Mean<br>SEM | 47781.85^^<br>2777.89 | 30.12<br>0.65 | 1489.34^<br>95.23 |
| | Compound 9 (1 mg/kg, p.o.) | Mean<br>SEM | 51421.60<br>2759.16 | 30.67<br>0.66 | 1619.28<br>96.01 |
| | Compound 9 (3 mg/kg, p.o.) | Mean<br>SEM | 48347.97^<br>3002.61 | 29.97<br>0.75 | 1503.53<br>102.46 |
| | Compound 9 (10 mg/kg, p.o.) | Mean<br>SEM | 53382.85<br>2451.57 | 31.99<br>0.70 | 1755.96<br>89.20 |
| Day-3 | Vehicle (2 mL/kg, p.o) | Mean<br>SEM | 24898.10*<br>2855.42 | 21.50*<br>0.71 | 576.09***<br>73.16 |
| | Scopolamine (0.5 mg/kg, s.c.) | Mean<br>SEM | 51356.46<br>2843.63 | 32.77<br>0.59 | 1727.72<br>99.42 |
| | Donepezil (3 mg/kg, s.c.) | Mean<br>SEM | 37535.77<br>3516.51 | 30.75<br>0.85 | 1168.44*<br>111.90 |
| | Compound 9 (1 mg/kg, p.o.) | Mean<br>SEM | 43128.23<br>3469.37 | 31.07<br>0.89 | 1414.4745^<br>122.33 |
| | Compound 9 (3 mg/kg, p.o.) | Mean<br>SEM | 32780.27<br>3646.14 | 28.45<br>1.03 | 1038.10**<br>126.01 |
| | Compound 9 (10 mg/kg, p.o.) | Mean<br>SEM | 45171.54<br>3358.79 | 30.89^<br>0.91 | 1509.45<br>119.36 |
| Day-4 | Vehicle (2 mL/kg, p.o) | Mean<br>SEM | 21939.72*<br>2501.90 | 21.57*<br>0.62 | 475.66<br>56.11 |
| | Scopolamine (0.5 mg/kg, s.c.) | Mean<br>SEM | 47889.29<br>3146.50 | 32.74<br>0.58 | 1573.41<br>108.41 |
| | Donepezil (3 mg/kg, s.c.) | Mean<br>SEM | 30444.375*<br>3333.25 | 32.34<br>0.68 | 1003.127*<br>113.98 |
| | Compound 9 (1 mg/kg, p.o.) | Mean<br>SEM | 40643.54<br>3435.86 | 29.51*<br>1.00 | 1233.92*<br>115.11 |
| | Compound 9 (3 mg/kg, p.o.) | Mean<br>SEM | 31915.04*<br>3377.04 | 28.57*<br>0.65 | 946.10***<br>106.14 |
| | Compound 9 (10 mg/kg, p.o.) | Mean<br>SEM | 40663.06<br>3350.15 | 29.36**<br>0.75 | 1254.41^<br>111.67 |

COMPOUND 9 Treatment Causes Aβ Peptide Lowering in the Tg2576 Mouse Model

Treatment of Tg 2576 mice for 4 weeks with compound 9 (50 mg/kg dose orally daily) reduced brain levels of soluble aβ-42 and aβ-40 by 22 and 23% respectively. This reduction demonstrates the ability of this compound to lower the two pathogenic peptides associated with alzheimer's disease suggest the therapeutic effect of this compound.

Example 16

Effect of Compound #9 in Treatment of Multiple Sclerosis (MS)

Experimental autoimmune encephalomyelitis (EAE) is a $CD4^+$ T cell-mediated autoimmune disease which is characterized by an initial perivascular CD4+ T cell and mononuclear cell inflammation. There is a subsequent primary demyelination of axonal tracks in the central nervous system (CNS), which leads to progressive hind-limb paralysis. EAE is generally considered to be a relevant model for the human immune-mediated demyelinating disease multiple sclerosis (MS). *Mycobacterium tuberculosis* (Mt) and pertussis toxin (PT) are commonly mixed with neuro-proteins/peptides to induce EAE effectively. Injection of the peptide corresponding to the immunodominant epitope of myelin oligodendrocyte glycoprotein peptide ($MOG_{35-55}$) in C57BL/6 mice along with PT results in a chronic progressive form of EAE. Briefly, $MOG_{35-55}$ (a synthetic peptide) is emulsified in Complete Freund's Adjuvant (CFA) and injected subcutaneously on day 0. To increase permeability of the blood brain barrier, PT is given as IP injection on day 0 and day 2. The disease onset is typically observed between days 8 and 10 with the peak occurring between days 13 and 15. Thereafter, the severity of the disease persists with mild variation. This animal model is characterized by initial tail paralysis followed by hind limb paralysis and further progression to forelimb paralysis. Increase in severity of the disease can also result in respiratory paralysis and death. The potent activities of new chemical entities (NCE) are evaluated in this model which translates well into the human clinical management of multiple sclerosis (MS). Fingolimod (FTY-720) (Cayman Chemical, Prolab Marketing) is a first-in-class orally bioavailable compound that has shown efficacy in advanced clinical trials for the treatment of MS and is used herein as a standard control at a dosage of 3 mpk, P.O, OD, from day 0 to day 42.

Method

Female C57BL/6 mice weighing about 19-22 g and 8-9 weeks old were induced multiple sclerosis by known method and as described above. Compound #9 was given at a dosage of 20 & 40 mpk, OD, P.O from day 0 to 42 at a dose volume of 10 ml/kg. The vehicle used was 0.5% (w/v) sodium carboxy methylcellulose (medium viscosity) and 1% (v/v) Tween® 80 in Milli-Q® water. The experimental groups are given in Table 4.

TABLE 4

Experimental Groups for EAE

| Groups | Dose and treatment regimen | Immunization | n |
|---|---|---|---|
| Gp1. Sham control | No Dose | IFA emulsion | 5 |
| Gp2. EAE control | No Dose | MOG in CFA + PT | 10 |
| Gp3. FTY-720 @ 2mpk | 2mpk, QD for 42 days, PO | MOG in CFA + PT | 10 |
| Gp4. Compound 9 @ 20mpk | 20mpk, QD for 42 days, PO | MOG in CFA + PT | 10 |
| Gp5. Compound 9 @ 40mpk | 40mpk, QD for 42 days, PO | MOG in CFA + PT | 10 |

Clinical Score

From day 7 to day 42, signs and symptoms of EAE severity was assessed and the clinical scores were determined. The animals were scored (an increment by 0.5) based on the criteria given below:

Score 0—Normal mouse; no overt signs of disease
Score 1—Partial tail paralysis
Score 2—Complete tail paralysis
Score 3—Unilateral hind limb paralysis
Score 4—Bilateral hind limb paralysis
Score 5—Urinary incontinence, moribund, death by EAE; Euthanized Histopathology Spinal cord was collected on day 42 in 10% Buffered Neutral Formalin. The tissues were processed under routine histopathological processing and followed by embedding and sectioning. The 4-5µ thick sections (spinal cord) were stained with H&E and luxol fast blue staining to assess the inflammation.

Six cross sections of spinal cord stained with H&E from each animal were evaluated for cellular infiltration and the severity of inflammation was assessed on a scale of 0 to 4 as given in Table 5.

TABLE 5

Scoring for H & E Staining

| Score | Observation |
|---|---|
| 0 | Normal |
| 1 | Mild infiltration of inflammatory cells surrounding blood vessels |
| 2 | Moderate inflammatory cell infiltration |
| 3 | Severe inflammatory cell infiltration invading the white matter |
| 4 | Very severe inflammatory cell infiltration spreading across white and grey matter |

Six cross sections of spinal cord stained with Luxol Fast Blue (LFB) were assessed for the severity of demyelination using similar score (in a scale of 0 to 4, Table 6).

TABLE 6

Scoring for LFB Staining

| Score | Observation |
|---|---|
| 0 | Normal |
| 0.5 | Traces of perivascular or subpial demyelination |
| 1 | Marked perivascular or subpial demyelination |
| 2 | Confluent perivascular or subpial demyelination |
| 3 | Massive confluent demyelination |
| 4 | Extensive demyelination |

Results

Clinical Score

Figure 3:
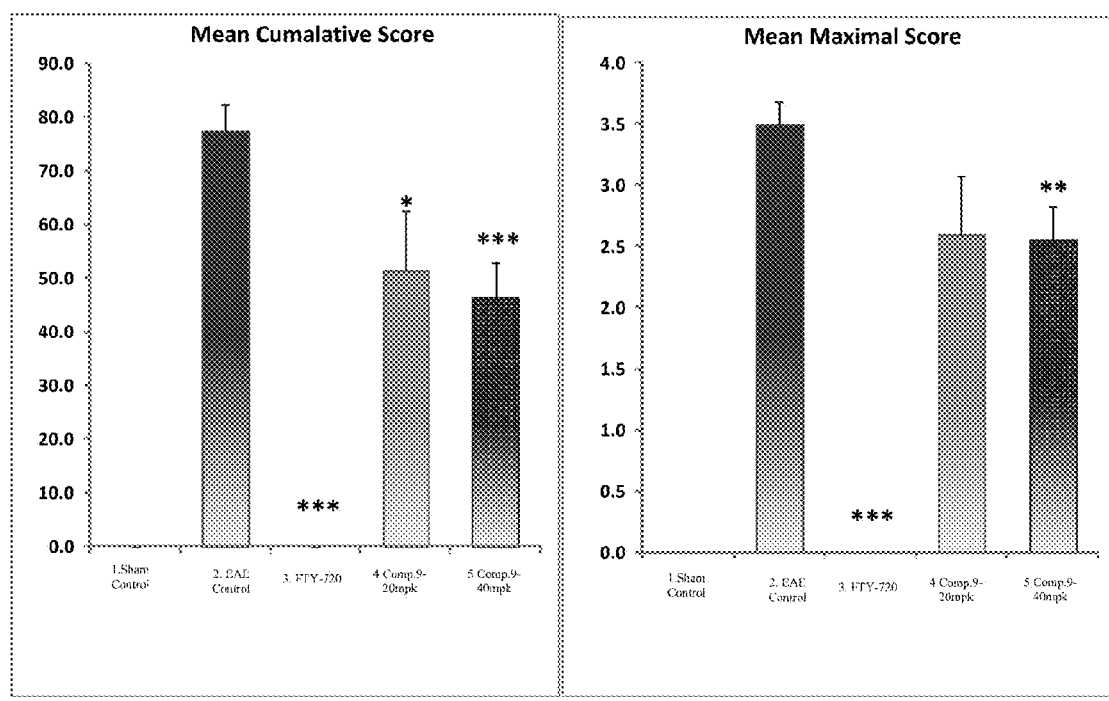
FIG. 3. Mean maximum clinical score and Cumulative clinical score is the internal identifier of Compound #9.

Mean cumulative clinical scores of Compound #9 at 20 and 40 mpk were significantly reduced when compared to EAE control group with P<0.05 and P<0.011 respectively (FIG. 3), whereas mean maximal clinical score of Compound #9 at 40 mpk was significantly reduced (p<0.01) when compared to EAE control. FTY-720 treated animals did not show any clinical score and comparable to sham control (FIG. 3).

Histopathology Score

Figure 4:
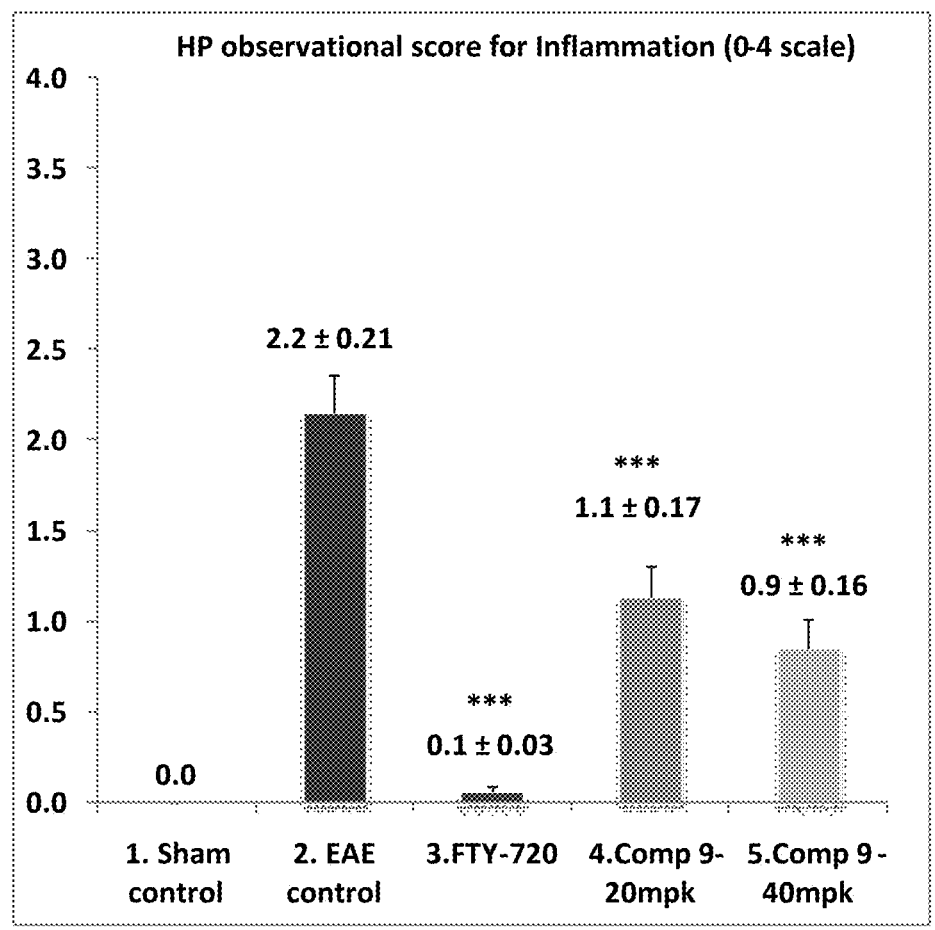
FIG. 4: H&E Inflammation score is the internal identifier of Compound #9

H & E Staining (for Inflammation) of Spinal Cord (FIG. 4):

The photographs of sham control mice showed normal architecture of spinal cord with white matter present in the periphery and grey matter in the centre. Normal distribution of myelin around the axons in white matter was observed. The photomicrograph of EAE control mice showed presence of large number of inflammatory cells invading the white matter as well as grey matter from the blood vessels. Whereas FTY-720 treated animals showed complete absence or very few inflammatory cells in the white matter around the blood vessels only. The photomicrograph of Compound #9 (20 mpk) treated mice showed presence of inflammatory cells in the white matter as well as grey matter. However, when compared to EAE control, the inflammatory cell infiltration was considerably low. The photomicrograph of Compound #9 (40 mpk) treated mice showed very few inflammatory cells in the white matter as well as grey matter. When compared to EAE control, the inflammatory cell infiltration was considerably low.

Figure 5:
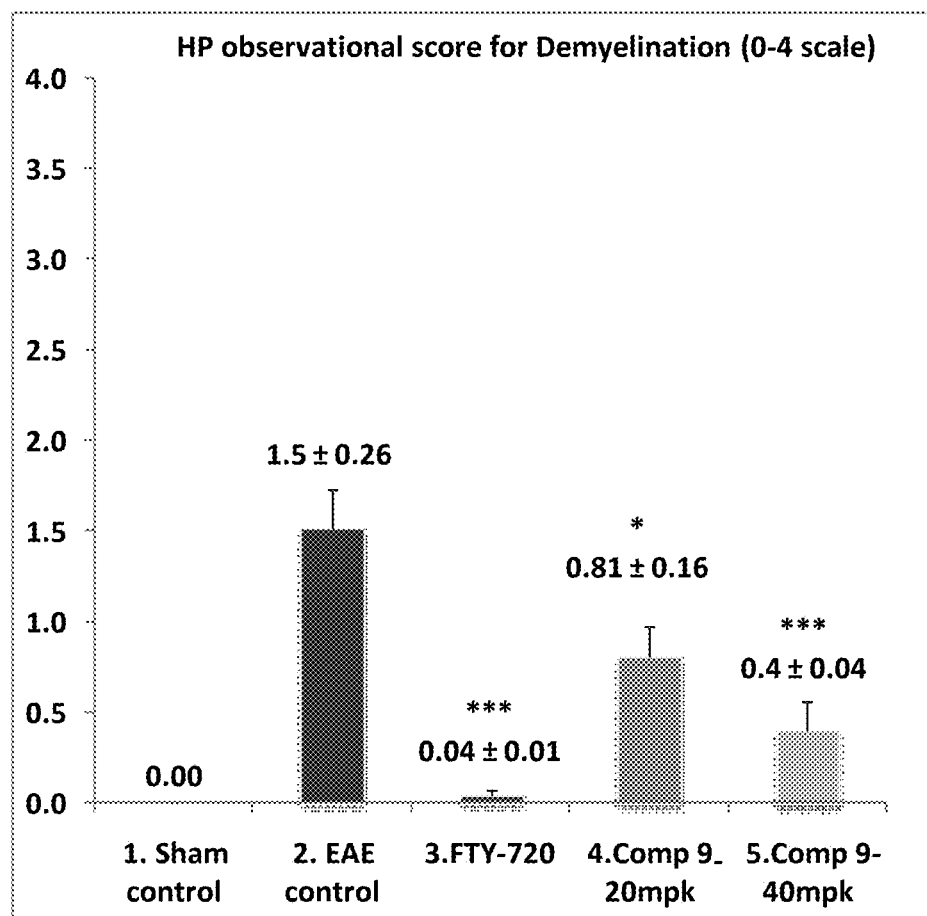
FIG. 5: Luxol fast blue (Demyelination) score is the internal identifier of Compound #9.

Luxol Fast Blue Staining (for Demyelination) of Spinal Cord (FIG. 5):

Spinal cord sections of EAE control mice showed presence of focal areas of demyelination in the white matter. FTY-720 treated mice showed complete absence or very few area of demyelination in the white matter around the blood vessels. Mice treated with Compound #9 (20 mpk) showed considerable presence of demyelination around blood vessels and subpial area in the white matter. Mice treated with Compound #9 (40 mpk) showed very few areas of demyelination in the white matter and the extent of demyelination was mostly restricted around the blood vessels.

Mice treated with Compound #9 showed dose dependent reduction in clinical scores, reduced inflammatory cells in white and grey matter of spinal cord. Compound #9 inhibited demyelination of spinal cord significantly at highest dose tested.

We claim:

1. A compound of Formula I:

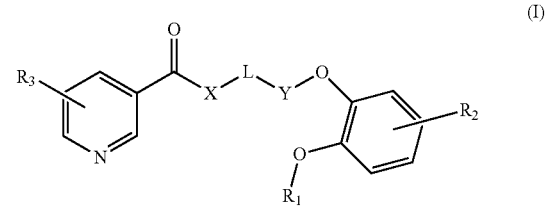

(I)

wherein,

X is selected from O, and NR";
L is a bond, or a substituted or unsubstituted C1-4 alkylene, wherein the substituents are selected from Ra;

X and L together with their attached positions form a five membered heterocyclyl, where in heterocyclyl is

Y is a bond, —C(O)—, or —S(O)$_2$—;
R$_1$ is CH$_3$;
R$_2$, is selected from H or C2-C3 alkenyl;
R$_3$ is H; and
Ra is selected from H, OR', C(O)2R', C(O)R', NR', N(NR")NR', SR', SO2R', SO2NR', NSO2R', C(O)NR', (CH2)nOR', (CH2)nSR', substituted or unsubstituted C1-C6 alkyl, wherein substituent is selected from OMe, S-Me, isopropyl, isobutyl —(CH2)n-Ph, —(CH2)n-Ph-OMe or —(CH2)n-indole,

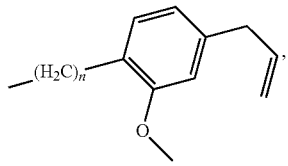

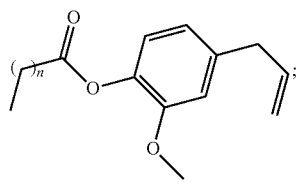

R' and R" are independently selected from H, substituted or unsubstituted alkyl, substituted or unsubstituted aryl, substituted or unsubstituted cycloalkyl, or substituted or unsubstituted heterocyclyl;

n is an integer 0-5.

2. The compound of claim 1, wherein the compound is a member selected from the group consisting of:

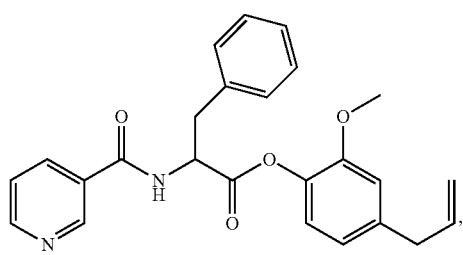

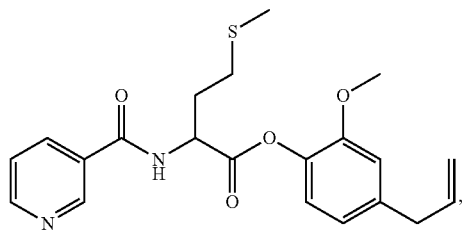

-continued

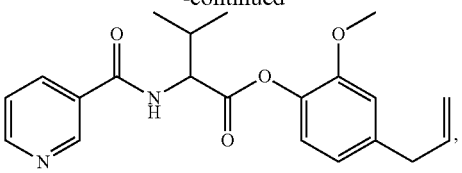

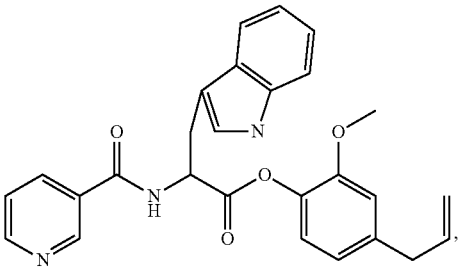

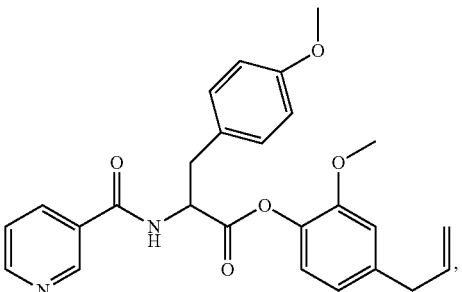

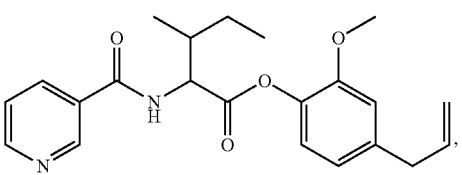

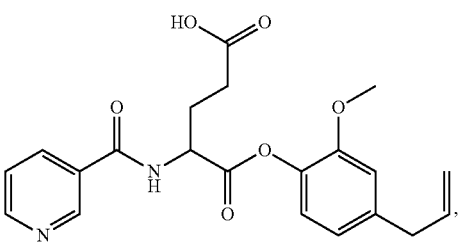

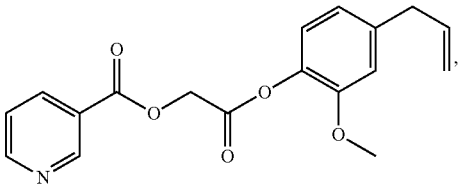

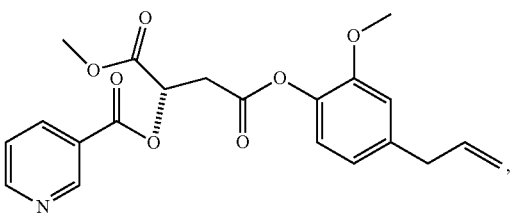

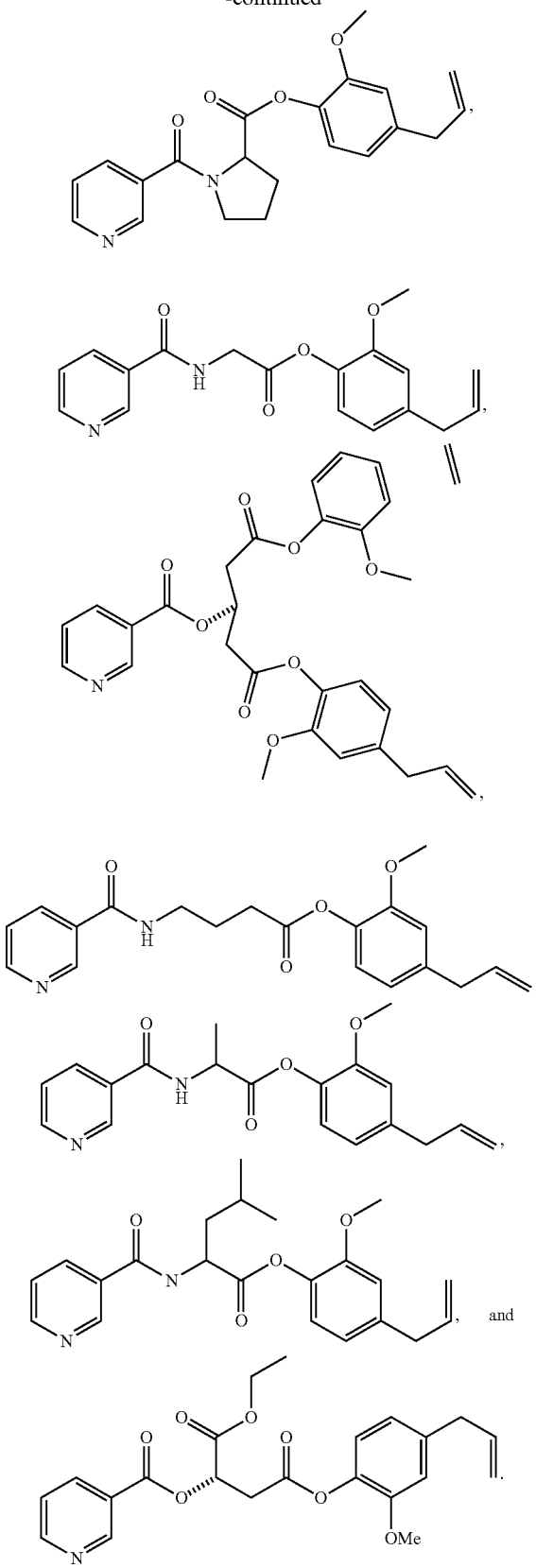

3. The compound of claim 1, wherein the compound is a member selected from the group consisting of:

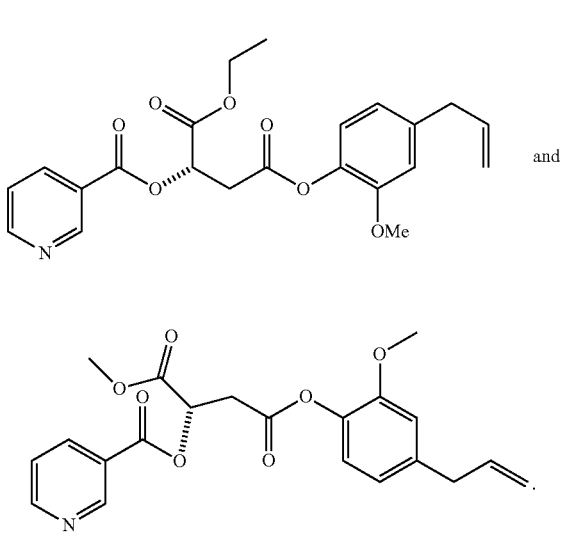

4. A compound selected from the group consisting of:

5. A pharmaceutical composition comprising therapeutically effective amount of a compound or a combination of compounds of claim 1, or a pharmaceutically acceptable salt form, stereoisomer or a ester thereof and a pharmaceutically acceptable carrier.

6. A method for lessening severity of Alzheimer's disease, dementia and neurodegenerative diseases selected from the group consisting of multiple sclerosis, ischemic stroke and Parkinson's disease, Fragile X Syndrome, Amyotropic Lateral Sclerosis, Huntington's disease wherein the said method comprises administering to a patient an effective amount of at least one of a compound or a combination of compounds of claim 1, or a pharmaceutically acceptable salt form, stereoisomer or a ester thereof, and wherein the compound is effective for lessening the severity of Alzheimer's disease, dementia and the neurodegenerative diseases.

7. The method of claim 6, wherein the compound is selected from:

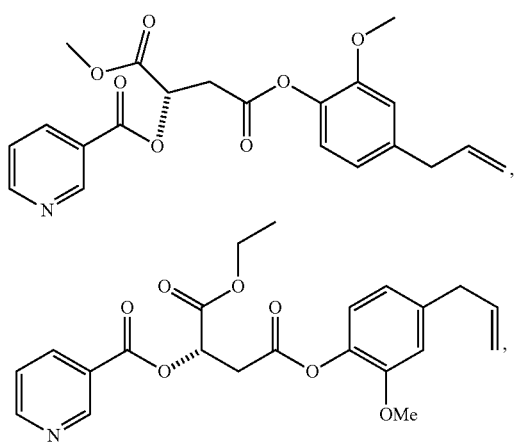
or a combination thereof, and wherein the compound is effective for lessening the severity of Alzheimer's disease, dementia and the neurodegenerative diseases.
8. The method of claim 6, wherein the compound is metabolized to:
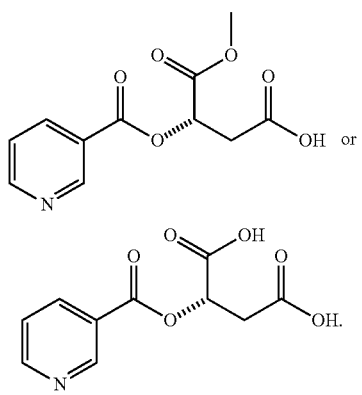
* * * * *